US009668601B1

(12) United States Patent
Rogers et al.

(10) Patent No.: US 9,668,601 B1
(45) Date of Patent: Jun. 6, 2017

(54) GLOVE DISPENSING DEVICE

(71) Applicants: Joe E. Rogers, Jonesboro, AR (US); David Onstead, Jonesboro, AR (US)

(72) Inventors: Joe E. Rogers, Jonesboro, AR (US); David Onstead, Jonesboro, AR (US)

(73) Assignee: GLOVE ASSIST, INC., Jonesboro, AR (US)

( * ) Notice: Subject to any disclaimer, the term of this patent is extended or adjusted under 35 U.S.C. 154(b) by 18 days.

(21) Appl. No.: 14/942,924

(22) Filed: Nov. 16, 2015

Related U.S. Application Data

(63) Continuation-in-part of application No. 14/201,853, filed on Mar. 8, 2014, now Pat. No. 9,186,012.

(60) Provisional application No. 61/775,313, filed on Mar. 8, 2013.

(51) Int. Cl.
*A47G 25/90* (2006.01)
*B25J 21/02* (2006.01)

(52) U.S. Cl.
CPC .......... *A47G 25/904* (2013.01); *A47G 25/90* (2013.01); *B25J 21/02* (2013.01)

(58) Field of Classification Search
CPC ....... A47G 25/90; A47G 25/904; B25J 21/02; A41D 19/00; A41D 19/0034; A41D 19/015; A41D 19/0044; A41D 19/0048; A61B 19/04
See application file for complete search history.

(56) References Cited

U.S. PATENT DOCUMENTS

| 3,323,846 | A | * | 6/1967 | Boddy | ..................... | B25J 21/02 2/270 |
| 3,695,493 | A | * | 10/1972 | Karr | ..................... | A47G 25/904 2/162 |
| 4,002,276 | A | * | 1/1977 | Poncy | ..................... | A61B 42/40 206/278 |
| 4,915,272 | A | * | 4/1990 | Vlock | .................. | A47G 25/904 206/278 |
| 5,058,785 | A | * | 10/1991 | Rich | ..................... | A47G 25/904 223/111 |
| 2003/0094468 | A1 | * | 5/2003 | Sinai | ..................... | A47G 25/904 223/111 |

* cited by examiner

*Primary Examiner* — Ismael Izaguirre
(74) *Attorney, Agent, or Firm* — Schrantz Law Firm, PLLC; Stephen D. Schrantz

(57) ABSTRACT

The glove dispensing device enables the placement of a glove on a glove retainer. The placement of the glove on the glove retainer at least partially seals the glove with the glove retainer. The user activates a vacuum that draws the glove into a housing of the glove dispensing device. The vacuum inverts the glove thus opening the glove to allow placement of the user's hand within the glove. The user may then remove his hand with the glove from the glove retainer. To assist with removing the glove from the glove retainer, the glove dispensing device provides a release toggle stored within the glove retainer. The user adjusts the release toggle to break the seal of the glove with the glove retainer. Breaking the seal overcomes the pressure applied to the glove from the vacuum. Thus, the glove is applied to the user's hand and ready for use.

20 Claims, 31 Drawing Sheets

GLOVE DISPENSING DEVICE

CROSS-REFERENCE TO RELATED APPLICATIONS

This application claims priority to and is a continuation in part of U.S. patent application Ser. No. 14/201,853 entitled "GLOVE DISPENSING DEVICE" filed on Mar. 8, 2014 which is a continuation in part of U.S. Patent Application No. 61/775,313 entitled "Medical Glove Dispenser and Inverter for Donning and Reducing the Risk of Germ Contact" filed on Mar. 8, 2013.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

1. Field of the Invention

The present invention relates generally to a glove dispensing device. The glove dispensing device provides multiple container inserts for storage of glove containers. The multiple inserts enable a user to store multiple containers of gloves. These containers may vary according to size of glove, type of glove, or brand of glove. The user may apply a glove to each glove retainer. The glove retainer is sized to allow the glove to be placed at least partially around the glove retainer to assist with inserting a user's hands into the glove. A vacuum forms inside of the glove dispensing device drawing the glove into the housing. Drawing the glove into the dispensing device forms an opening for placement of a user's hand into the glove.

In the known art, a user is required to manually place gloves on a user's hands. Manually applying gloves require time and effort. The present invention reduces the time needed to apply gloves by inverting the gloves and creating a vacuum that opens the glove for insertion of the user's hand into the glove.

The glove dispensing device of the present invention overcomes many disadvantages of the known art. The glove dispensing device provides beneficial features not found in currently available devices. In view of the foregoing, the glove dispensing device of the present invention is well suited for increasing efficiency, promoting cleanliness, and reducing time needed to apply a glove. Therefore, the present invention is needed to provide a more effective device for applying gloves to a user's hands.

II. Description of the Known Art

Patents and patent applications disclosing relevant information are disclosed below. These patents and patent applications are hereby expressly incorporated by reference in their entirety.

U.S. Pat. No. 6,832,708 issued to Sinai on Dec. 21, 2004 ("the '708 patent") teaches a glove donning system and method, the arrangement having typically a vacuum wand for grasping the outer skin of the cuff portion of a glove, after which the wand together with the glove is suitably transported to a vacuum chamber, where the cuff portion is aligned with the rim of the opening of the vacuum chamber. By grasping only the outer skin of the glove, the cuff portion taught by the '708 patent is opened to enable a deflated inflatable ring to be inserted into the cuff portion. The ring taught by the '708 patent is then inflated while positioned inside the cuff portion, which is thereby expanded until it touches the rim of the vacuum chamber. The rim taught by the '708 patent is provided with a suction ring capable of generating sufficient suction to keep the cuff of the glove pressed against the rim, at which point the inflatable ring may be deflated and removed. A vacuum taught by the '708 patent may then be applied to the chamber, inflating the glove and thus enabling a hand to be inserted thereinto. A donning device taught by the '708 patent may be fitted with a pair of such systems, one for each hand, and further provided with suitable means for stacking and delivering on demand one glove to each vacuum chamber.

SUMMARY OF THE INVENTION

The glove dispensing device of the present invention enables the placement of a glove on a glove retainer. The placement of the glove on the glove retainer at least partially seals the glove with the glove retainer. The user then activates a vacuum that draws the glove into a housing of the glove dispensing device. The vacuum inverts the glove thus opening the glove to allow placement of the user's hand within the glove. The user may then remove his hand with the glove from the glove retainer. To assist with removing the glove from the glove retainer, the glove dispensing device provides a release toggle stored within the glove retainer. The user adjusts the release toggle to break the seal of the glove with the glove retainer. Breaking the seal overcomes the pressure applied to the glove from the vacuum. Thus, the glove is applied to the user's hand and ready for use.

It is an object of the present invention to reduce the amount of time needed to apply gloves.

It is an object of the present invention to promote changing gloves more frequently.

It is also an object of the present invention to simplify access to gloves.

It is also an object of the present invention to promote a more sterile environment.

It is also an object of the present invention to reduce contamination of the gloves.

It is also an object of the present invention to reduce environmental contamination of the gloves.

It is also an object of the present invention to promote efficiency.

It is also an object of the present invention to store an assortment of gloves for use within close proximity of the device.

These and other objects and advantages of the present invention, along with features of novelty appurtenant thereto, will appear or become apparent in the course of the following descriptive sections and the attached drawings.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views.

DETAILED DESCRIPTION

The present invention relates generally to a glove dispensing device 100. The glove dispensing device 100 of one embodiment provides a housing 101 capable of storing multiple containers of gloves. The housing may store the containers of gloves and a motor for creating a vacuum. The housing may be constructed from a plastic, metal, or other material.

Figure 1:
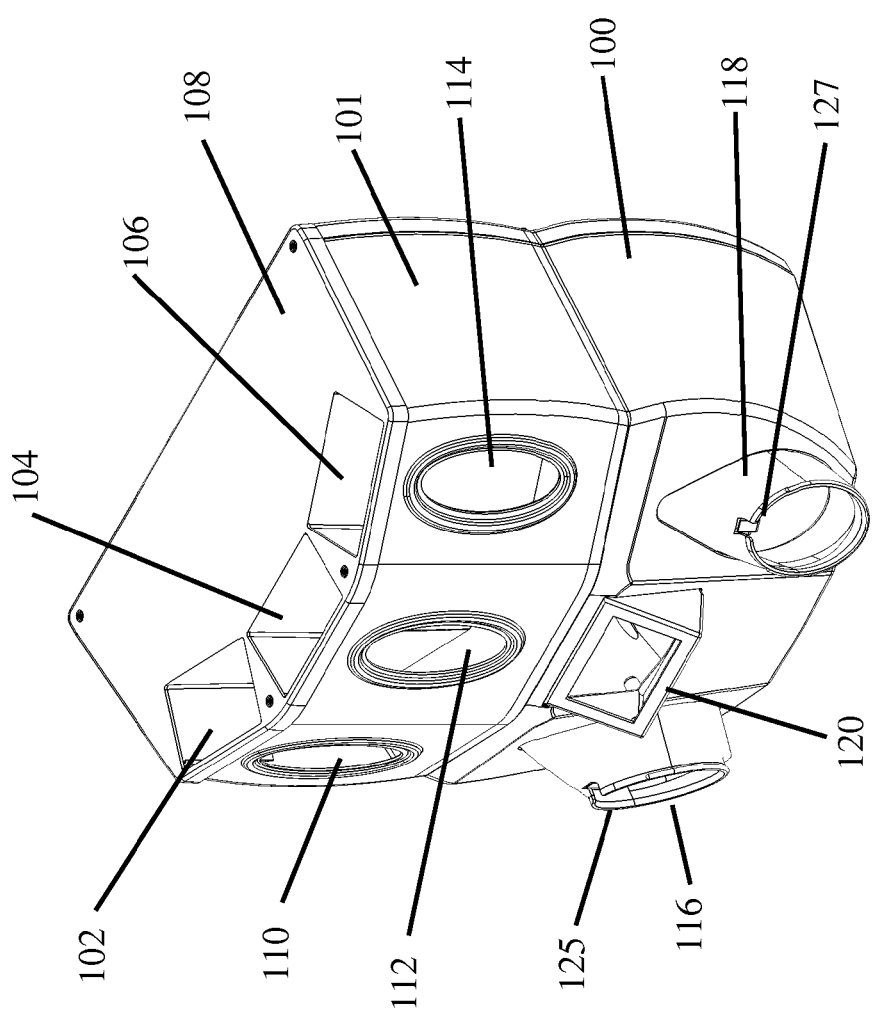
FIG. 1 is a perspective view showing one embodiment of the present invention.
Figure 2:
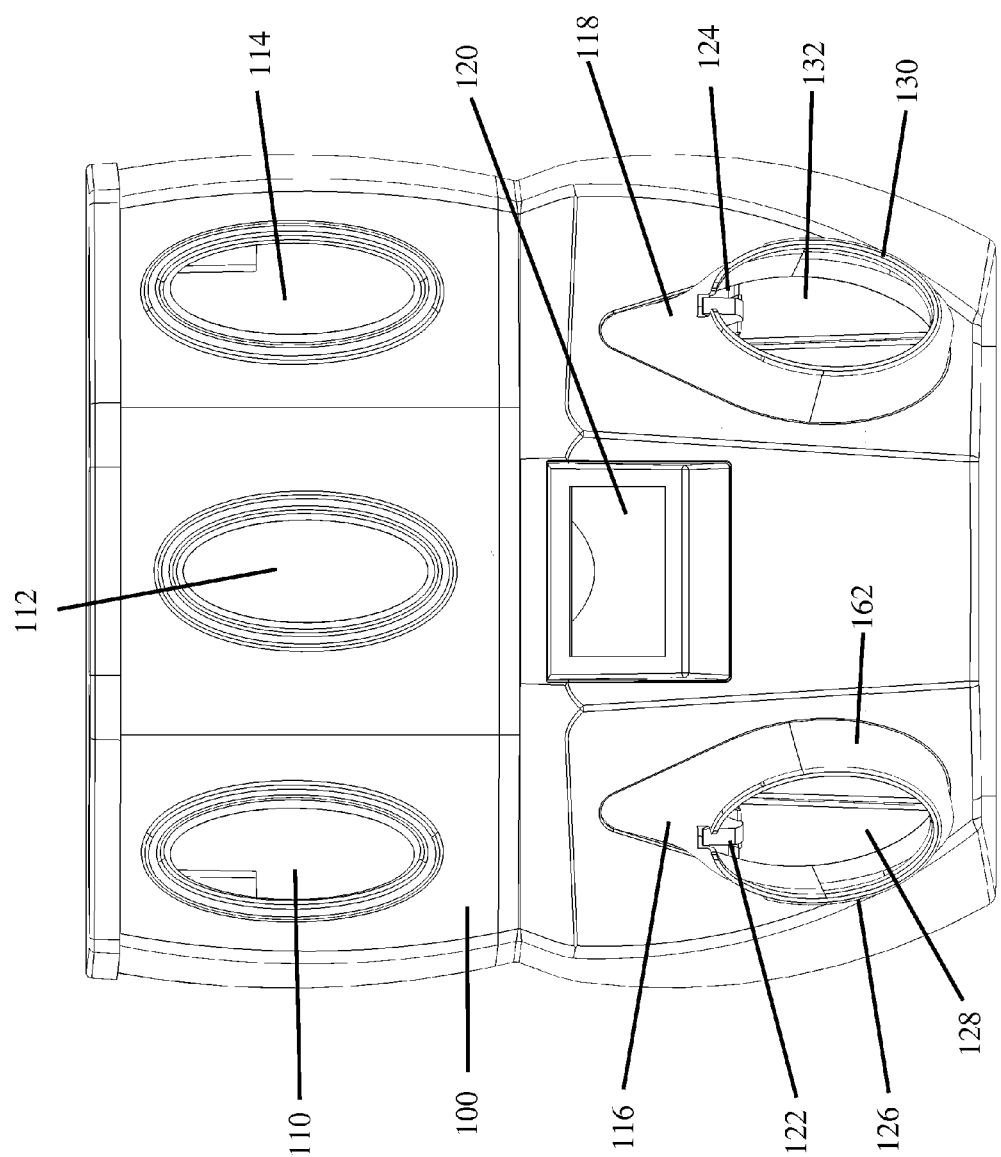
FIG. 2 is a front view thereof.

Referring to FIGS. 1 and 2, the housing 101 provides container inserts 102, 104, 106 for storage of the glove containers. The number of container inserts 102, 104, 106 may vary according to the needs of the user. The multiple inserts 102, 104, 106 enable a user to store multiple containers of gloves. These containers may vary according to size of glove, type of glove, and/or brand of glove. The user may store a different type and/or size of glove to each insert 102, 104, 106.

For example, if only one person will be using the dispensing device, one container insert may be used. If the user requires multiple types and/or sizes of gloves, the number of container inserts may be increased according to the user's needs. The container inserts 102, 104, 106 are top loaded from the top 108 of the housing 101.

Each container insert 102, 104, 106 provides a dispensing aperture 110, 112, 114. A user may access the gloves from the containers through the dispensing apertures 110, 112, 114. The dispensing apertures 110, 112, 114 are accessed through the side of the housing 101 to improve a user's access to the gloves within container inserts 102, 104, 106.

Two glove retainers 116, 118 protrude outward from the housing 101. The glove retainers 116, 118 accept a glove around the exterior of the glove retainers 116, 118. The placement of the glove on the glove retainer 116, 118 at least partially seals the glove with the glove retainer 116, 118. The user then activates a vacuum that draws the glove into the housing 101 of the glove dispensing device 100. The vacuum inverts the glove thus opening the glove to allow placement of the user's hand within the glove. The vacuum of one embodiment may be activated via control panel 120. In another embodiment, a sensor detects the user and activates the vacuum.

FIG. 2 provides more detailed information regarding the glove retainers 116, 118. Retainer apertures 128, 132 of each glove retainer 116, 118 enable passage into the housing 101. Lips 126, 130 extend outward from the retainer neck 162. The lips 126, 130 raise the surface of the glove retainers 116, 118 to reduce movement of the glove after the glove is applied on the glove retainers 116, 118.

The user applies the glove around the glove retainer 116, 118 to at least partially seal the retainer aperture 128, 132. When the vacuum is activated, the seal causes the glove to be drawn within the retainer aperture 128, 132. Thus, the vacuum inverts the glove. The lips 126, 130 limit the movement of the glove as it is drawn within the retainer aperture 128, 132. The lips 126, 130 maintain the glove on the glove retainer 116, 118 to prevent the glove from being drawn entirely into the housing.

As the user inserts his hand into the glove, the user may contact the release toggle 122, 124 to adjust the release toggle 122, 124. Adjustment of the release toggle 122, 124 contacts glove and breaks the seal between the glove and the retainer aperture 128, 132. The release toggle 122, 124 repositions the glove thus removing at least a portion of the glove from the glove retainer 116, 118. Once a portion of the glove is removed from the glove retainer 116, 118, the glove is released from the glove retainer 116, 118. The glove is then applied to the user's hand and ready for use.

Figure 3:
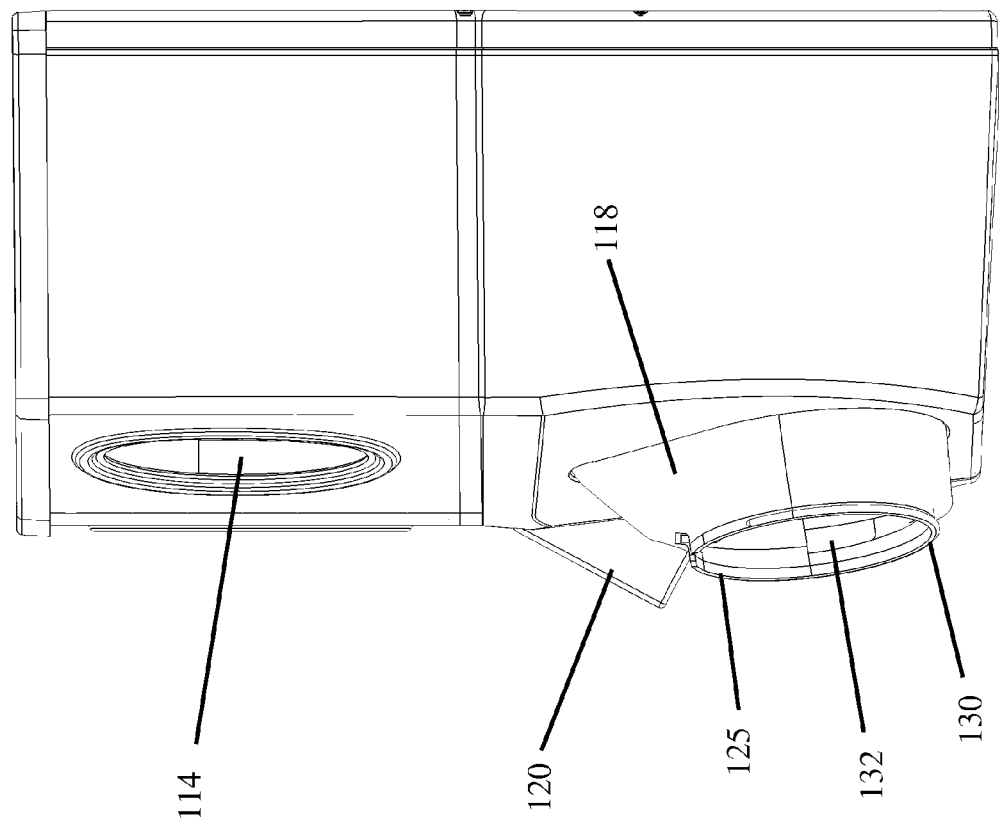
FIG. 3 is a right side view thereof, the left side view being a mirror image of the right side view.

FIG. 3 provides a side view of the glove dispensing device 100 and the glove retainer 118. Lip 130 at least partially encloses the retainer aperture 132.

Figure 4:
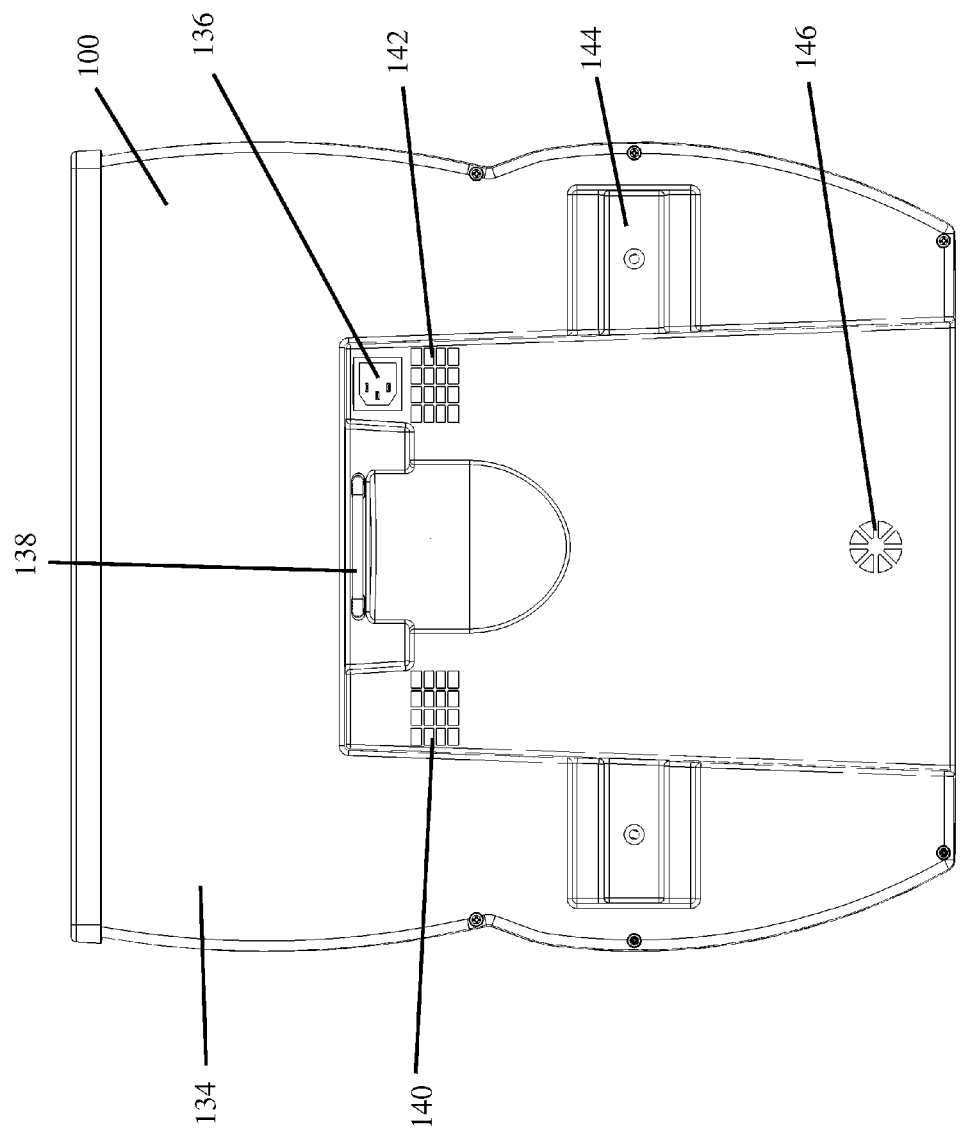
FIG. 4 is a rear view thereof.

FIG. 4 shows a rear view of the glove dispensing device 100. Power source 136 provides an electrical connection for powering the motor/vacuum, the control panel 120, and the glove dispensing device 100. Alternative power sources may be implemented with the present invention. The glove dispensing device may be operated via batteries, solar power, green power sources, alternative power sources, and other power sources.

Motor mount 138 of back 134 enables the motor to be mounted on the housing 101. The motor creates the vacuum by venting air through exhaust 140, 142. As will be described in greater detail below, the motor draws air from a vacuum chamber that is in fluid communication with retainer apertures 128, 132. The motor vents the air from vacuum chamber through exhausts 140, 142. To prevent a complete vacuum within the housing, the vacuum release 146 located at the vacuum chamber enables air into the vacuum chamber. The vacuum release 146 serves a safety valve to prevent walls of the housing 101 from collapsing during operation of the vacuum. The vacuum release 146 also assists with maintaining an appropriate pressure on the gloves to limit the gloves from being completely drawn within housing 101.

FIG. 4 also shows a mount 144 on back 134. The mount 144 enables wall mounting of the glove dispensing device 100 on a wall. A user may secure the glove dispensing device 100 via the mount 144 to simplify use of the glove dispensing device.

Figure 5:
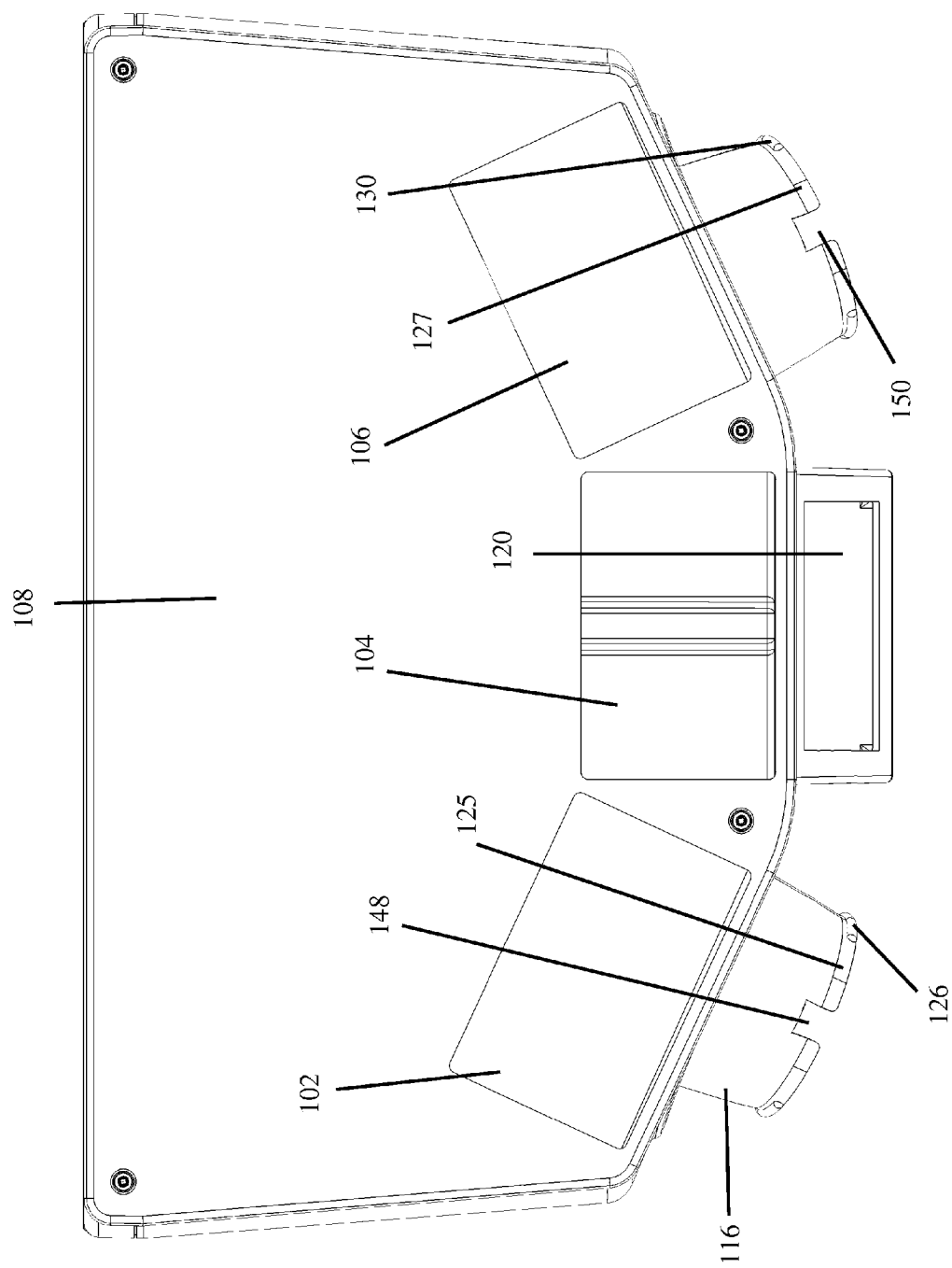
FIG. 5 is a top view thereof.

FIG. 5 shows a top view of the glove dispensing device 100. Container inserts 102, 104, 106 provide an aperture for storing a container of gloves. In one embodiment, the housing 101 provides for storage of three containers. The top view also shows control panel 120 that a user may access to activate the vacuum. The user may also access the control panel 120 to modify the settings of the vacuum as will be described below. The user may modify the speed of the motor and the run time of the motor to configure the pressure applied to the glove.

The top view shows toggle apertures 148, 150 of each glove retainer 116, 118. The collars 125, 127 define the retainer apertures 128, 132 and the toggle apertures 148, 150. Openings in collars 125, 127 form the toggle apertures 148, 150. The collars 125, 127 provide an external surface for securing the glove to the outer wall of the glove retainers 116, 118. Lips 126, 130 provide an extension outward from the outer wall of glove retainers 116, 118 to secure the gloves on the glove retainers 116, 118. Lips 126, 130 of one embodiment do not completely encompass the retainer aperture 128, 132 or collars 125, 127. In one embodiment, the collars 125, 127 provide a smooth surface without lips 126, 130 adjacent the toggle apertures 148, 150 to assist with releasing the gloves from the glove retainers 116, 118 adjacent the release toggles 122,124. The toggle aperture 148, 150 of one embodiment interrupts the continuity of the collars 125, 127 around the retainer aperture 128, 132.

Figure 6:
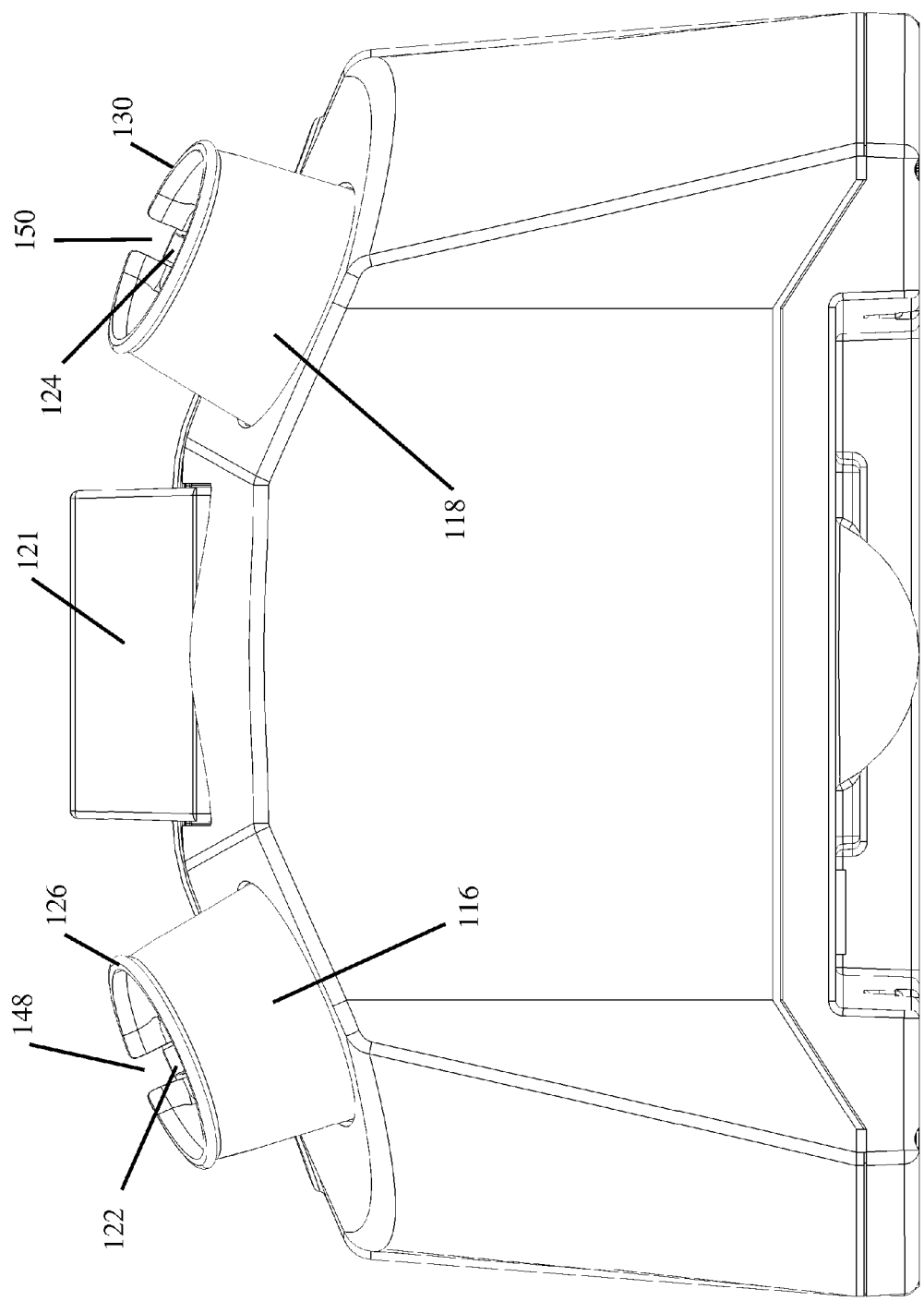
FIG. 6 is a rear view thereof.

FIG. 6 shows a bottom view showing the glove retainers 116, 118 extending outward from housing 101. The release toggles 122, 124 assist with removal of the gloves from glove retainers 116, 118. Sensor 121 of one embodiment activates the vacuum. In one embodiment, sensor 121 is a capacitive sensor that will activate the vacuum for a period of time.

Figure 7:
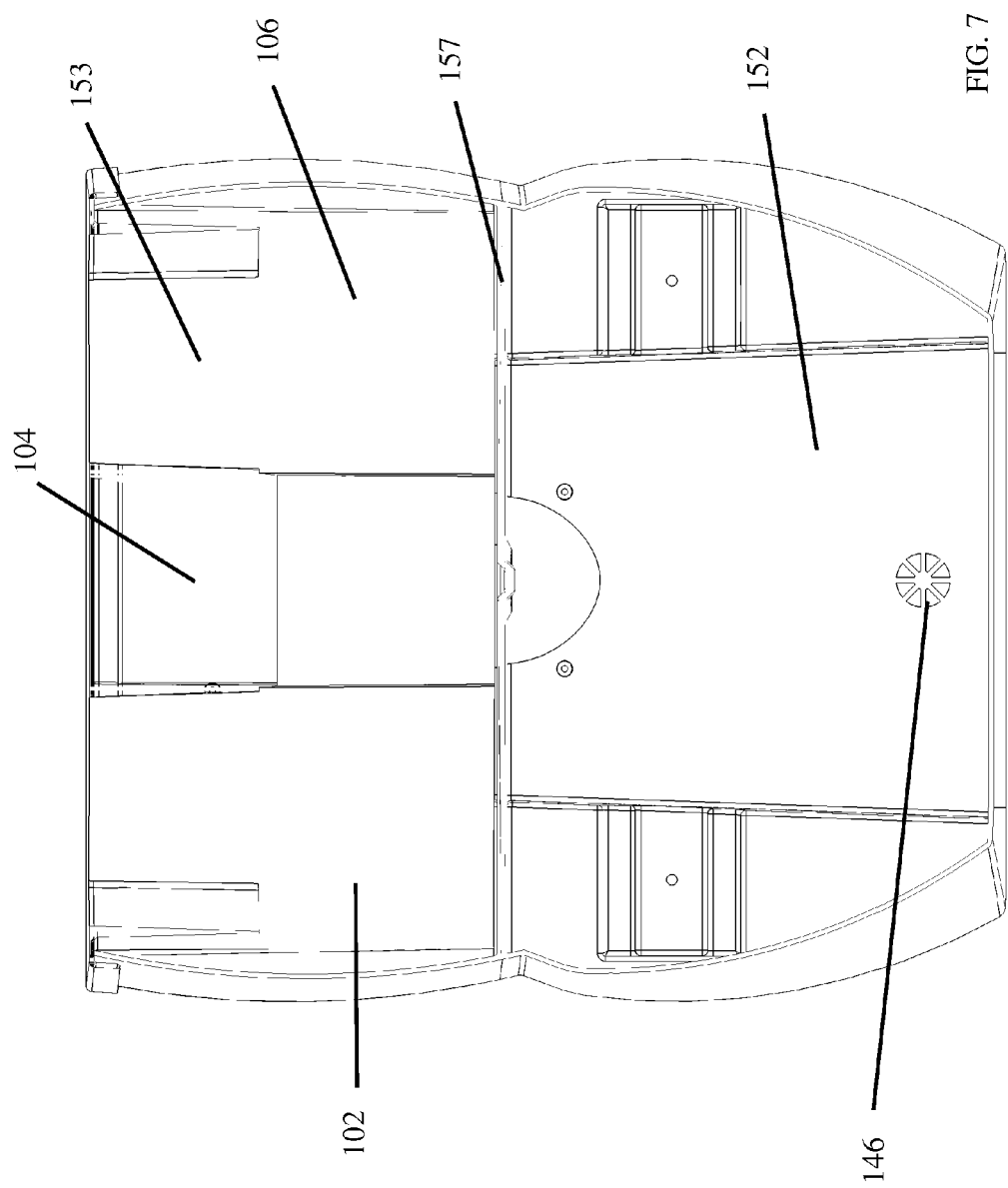
FIG. 7 is a sectional view thereof.

FIG. 7 shows a partial view of one embodiment of the present invention. The container inserts 102, 104, 106 are separated from the intake chamber 155 by wall 153. Vacuum chamber 152 is also separated from intake chamber 155 by divider 157. The vacuum chamber 152 is in fluid communication with retainer apertures 128, 132 such that gas may flow from retainer apertures 128, 132 through vacuum chamber 152 and through exhaust 140, 142.

Figure 8:
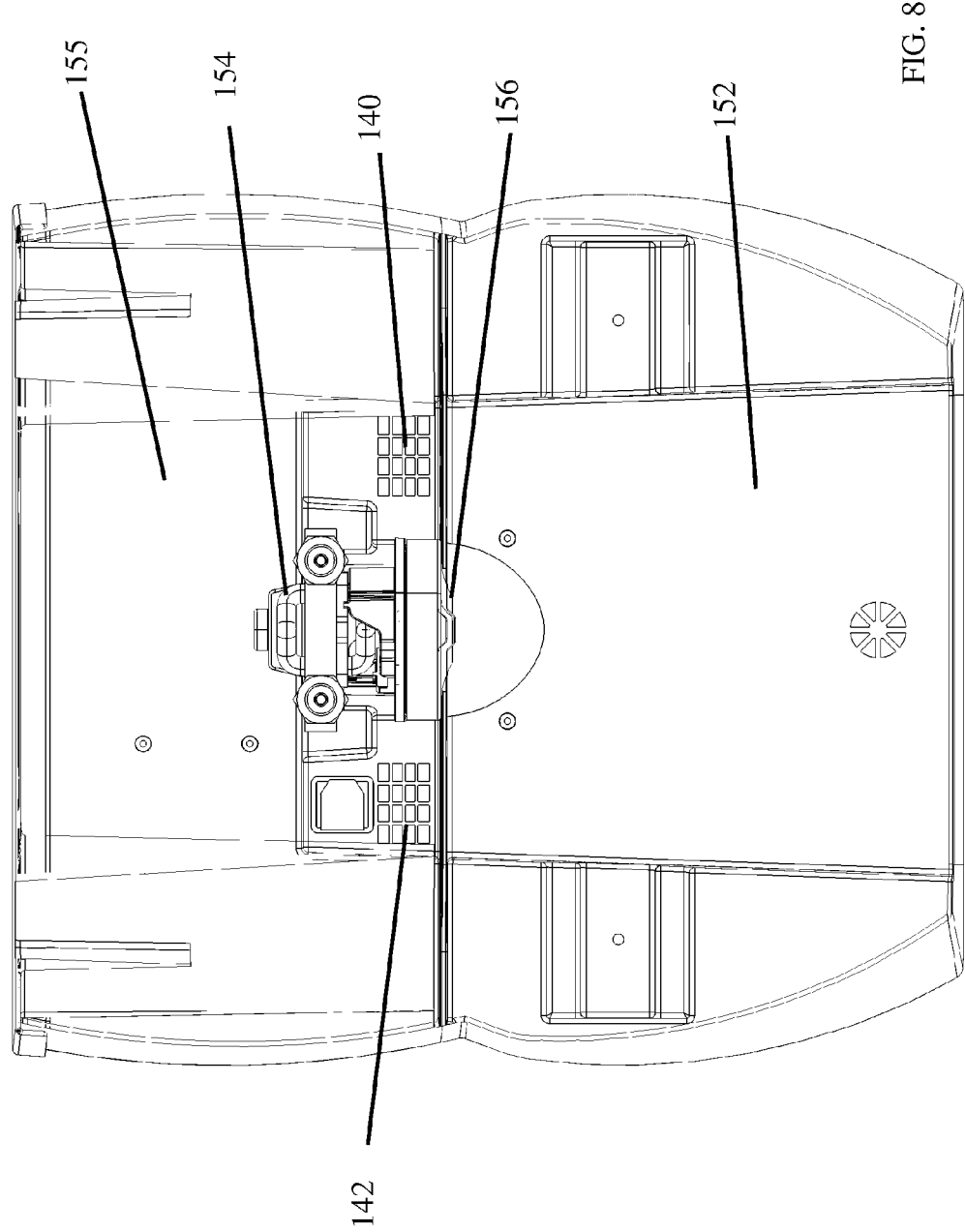
FIG. 8 is a sectional view thereof.
Figure 9:
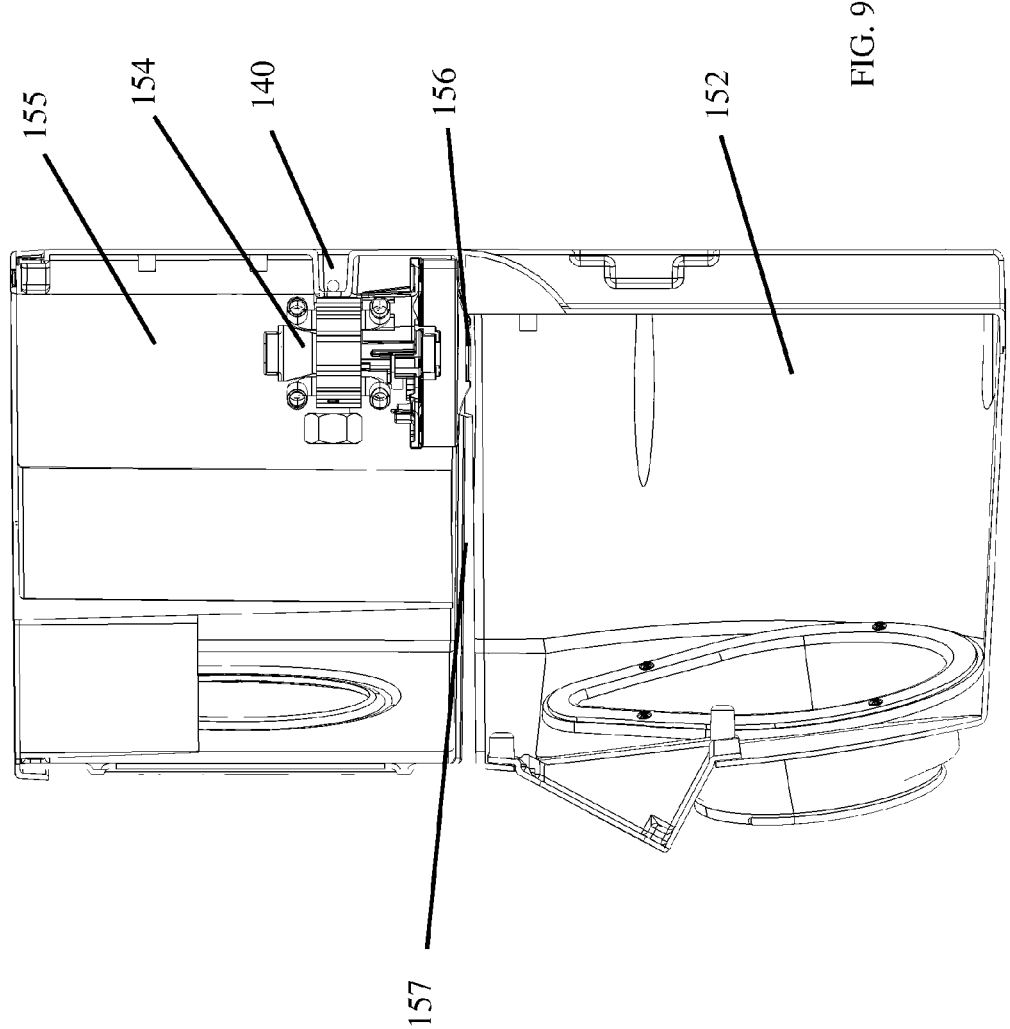
FIG. 9 is a sectional view thereof.
Figure 10:
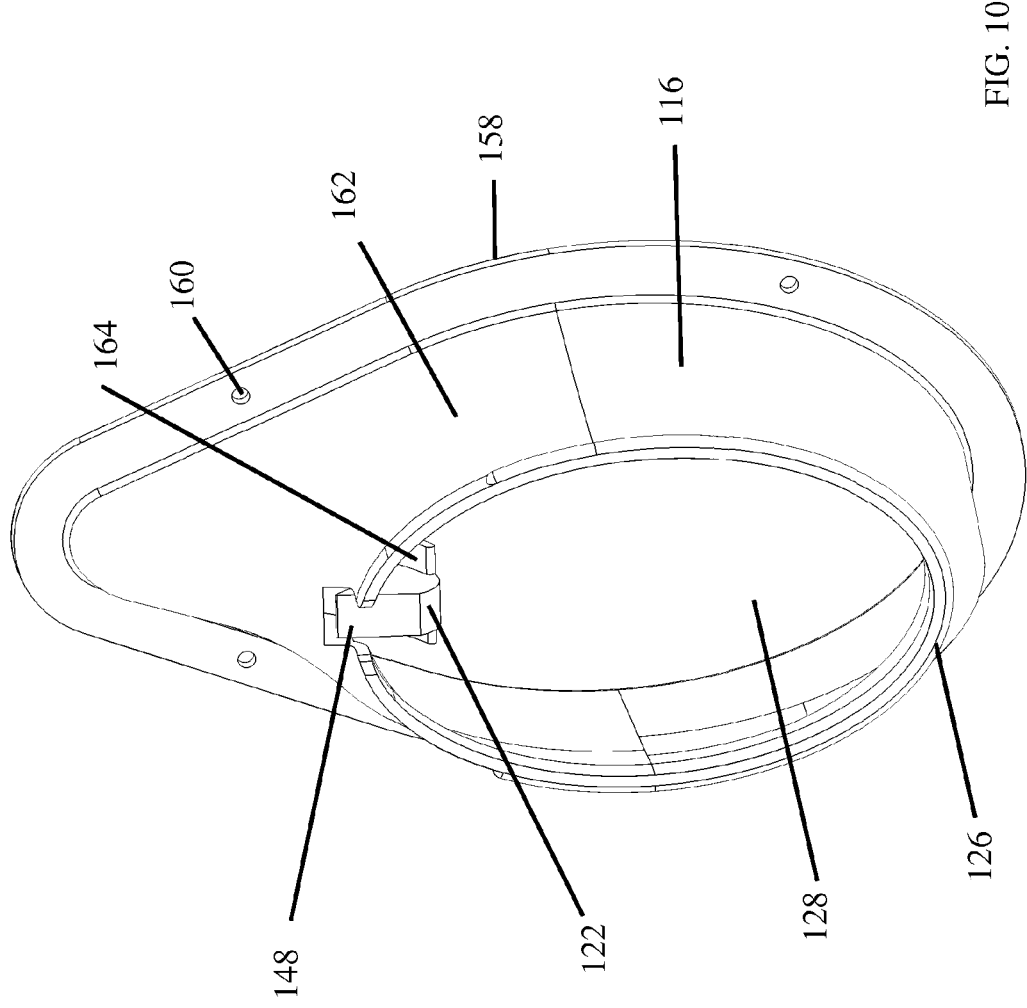
FIG. 10 is a perspective view of a glove receiver of one embodiment of the present invention.
Figure 11:
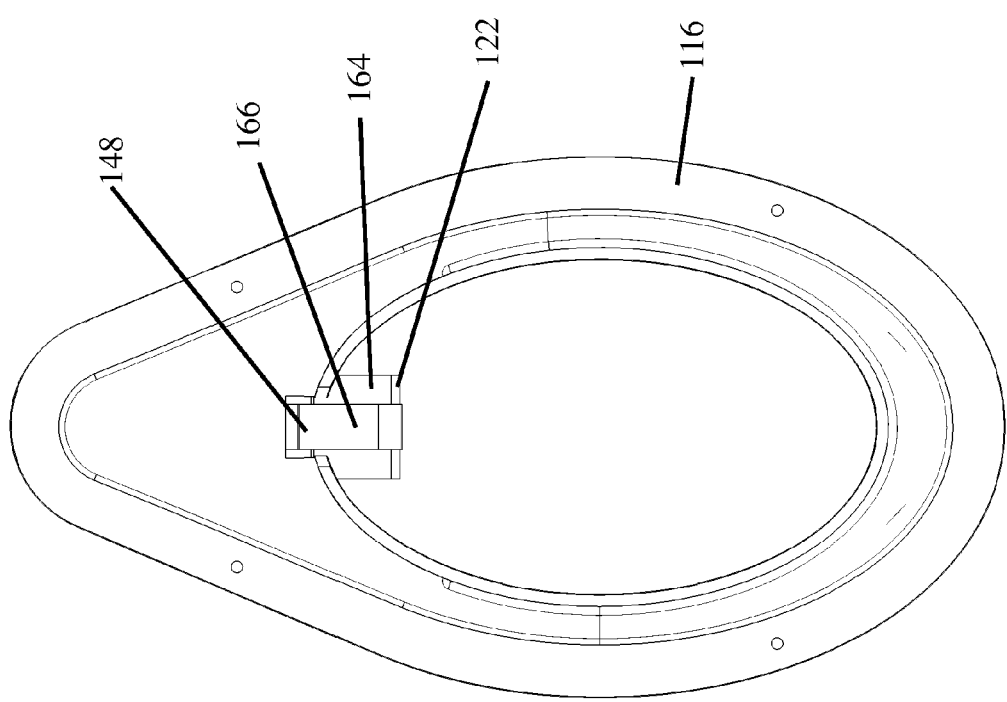
FIG. 11 is a front view thereof.
Figure 12:
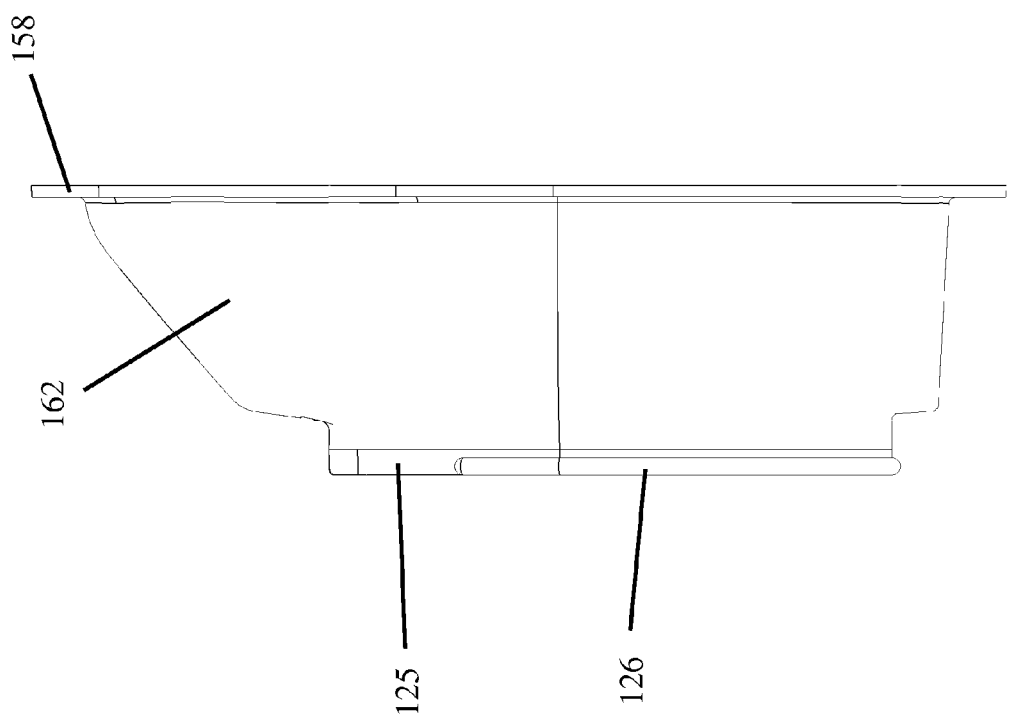
FIG. 12 is a right side view thereof, the left side view being a mirror image of the right side view.

FIGS. 8 and 9 show the intake chamber 155 and the vacuum chamber 152. In one embodiment, motor 154 mounted within intake chamber 155 draws gas from vacuum chamber 152. Divider 157 separates the vacuum chamber 152 from intake chamber 155. The motor 154 draws air from vacuum chamber 152 through intake 156 in divider 157. The motor 154 exhausts the air through the exhausts 140, 142.

FIGS. 10-15 show the glove retainer 116 in greater detail. Attachment shoulder 158 and attachment apertures 160 provide a surface of the glove retainer 116 to be attached to housing 101. In one embodiment, the glove retainer 116 is fastened to housing 101 by fasteners, such as screws, bolts, and/or other fasteners. The glove retainer 116 may be sonically welded to housing 101 or may be molded into the housing. The glove retainer 116 may be secured to housing 101 by other methods.

Release toggle 122 of one embodiment attaches to the glove retainer 116. The toggle head 166 of release toggle 122 is sized to pass through the toggle aperture 148. Toggle shoulder 164 extends from the sides of the toggle head 164 to limit movement of the release toggle 122. The toggle shoulder 164 prevents the release toggle 122 from completely passing through the toggle aperture 148.

Figure 13:
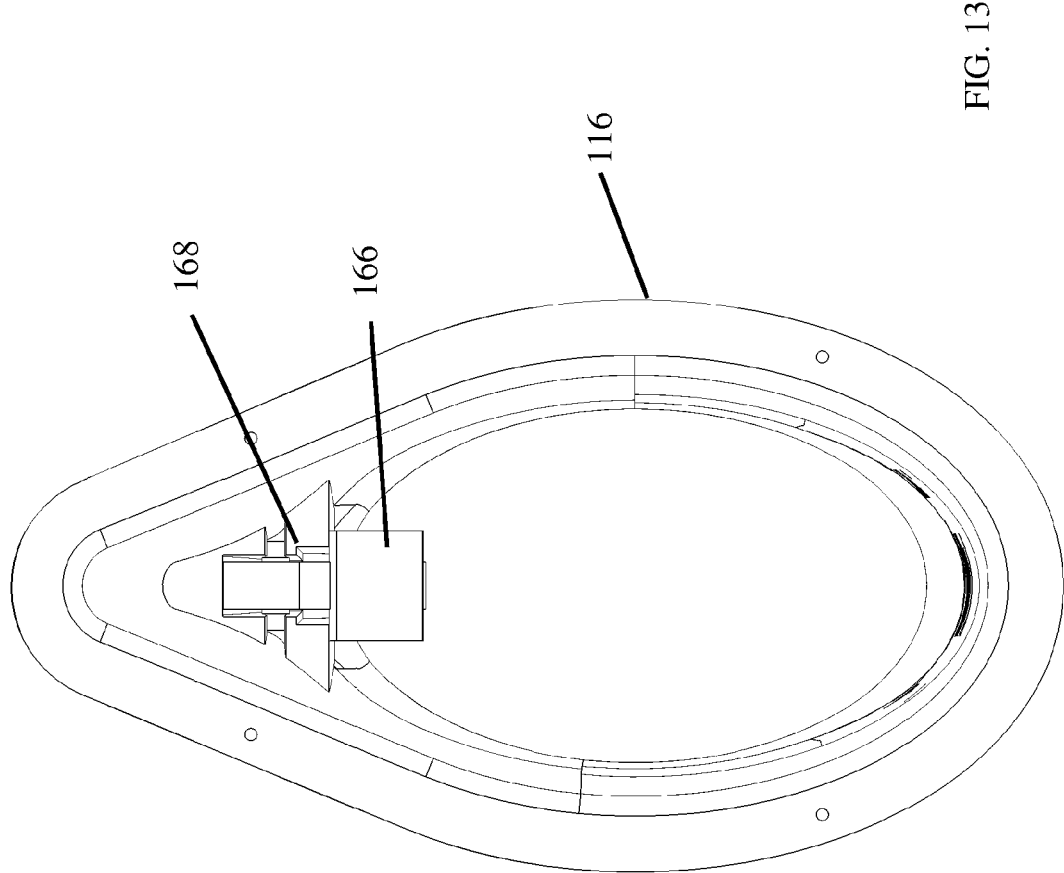
FIG. 13 is a rear view thereof.

FIG. 13 shows the back of the glove retainer 116. Toggle receiver 168 secures the release toggle 122 to the glove retainer 116. In one embodiment, the toggle receiver 168 is pivotally attached to the glove retainer.

Figure 14:
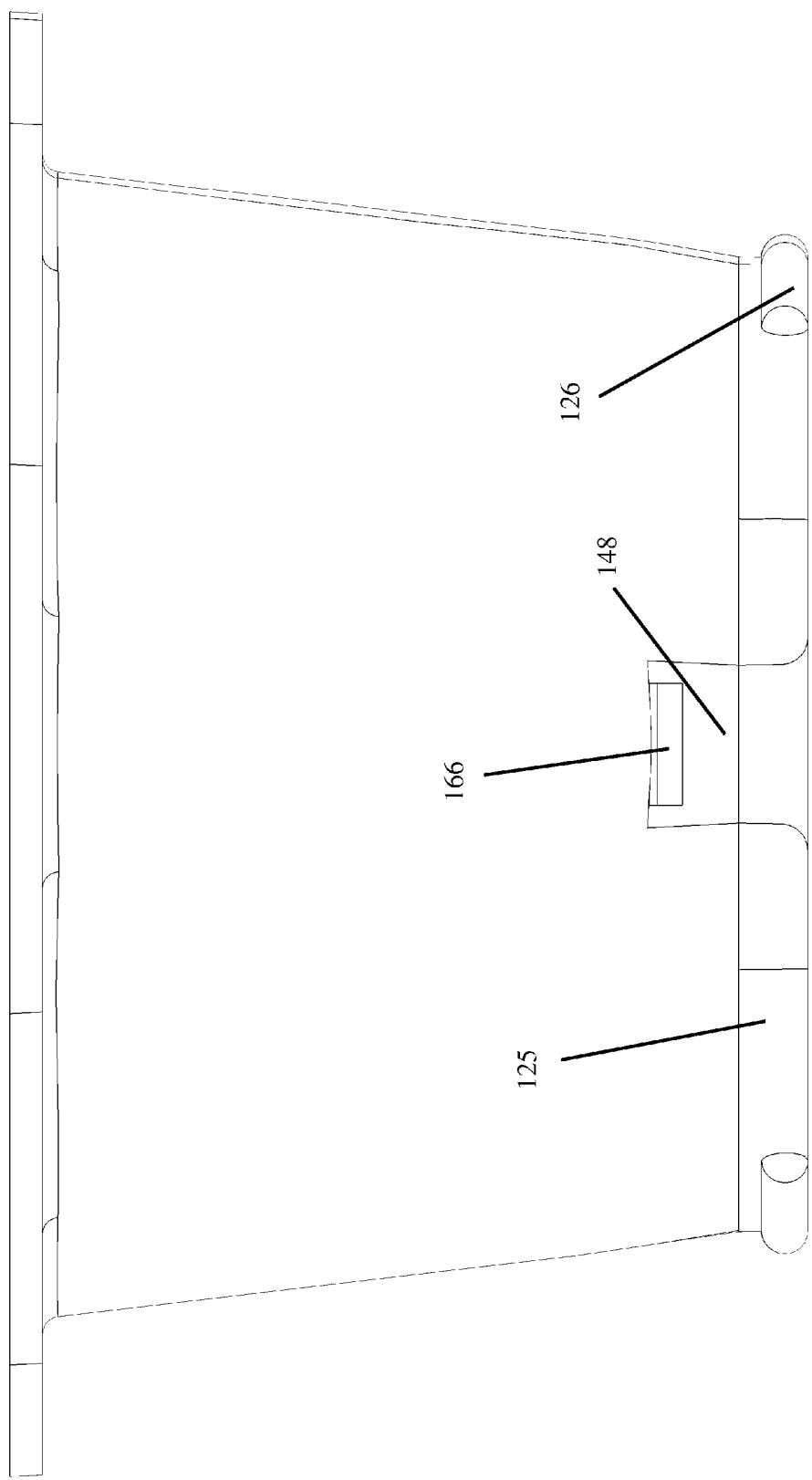
FIG. 14 is a top view thereof.
Figure 15:
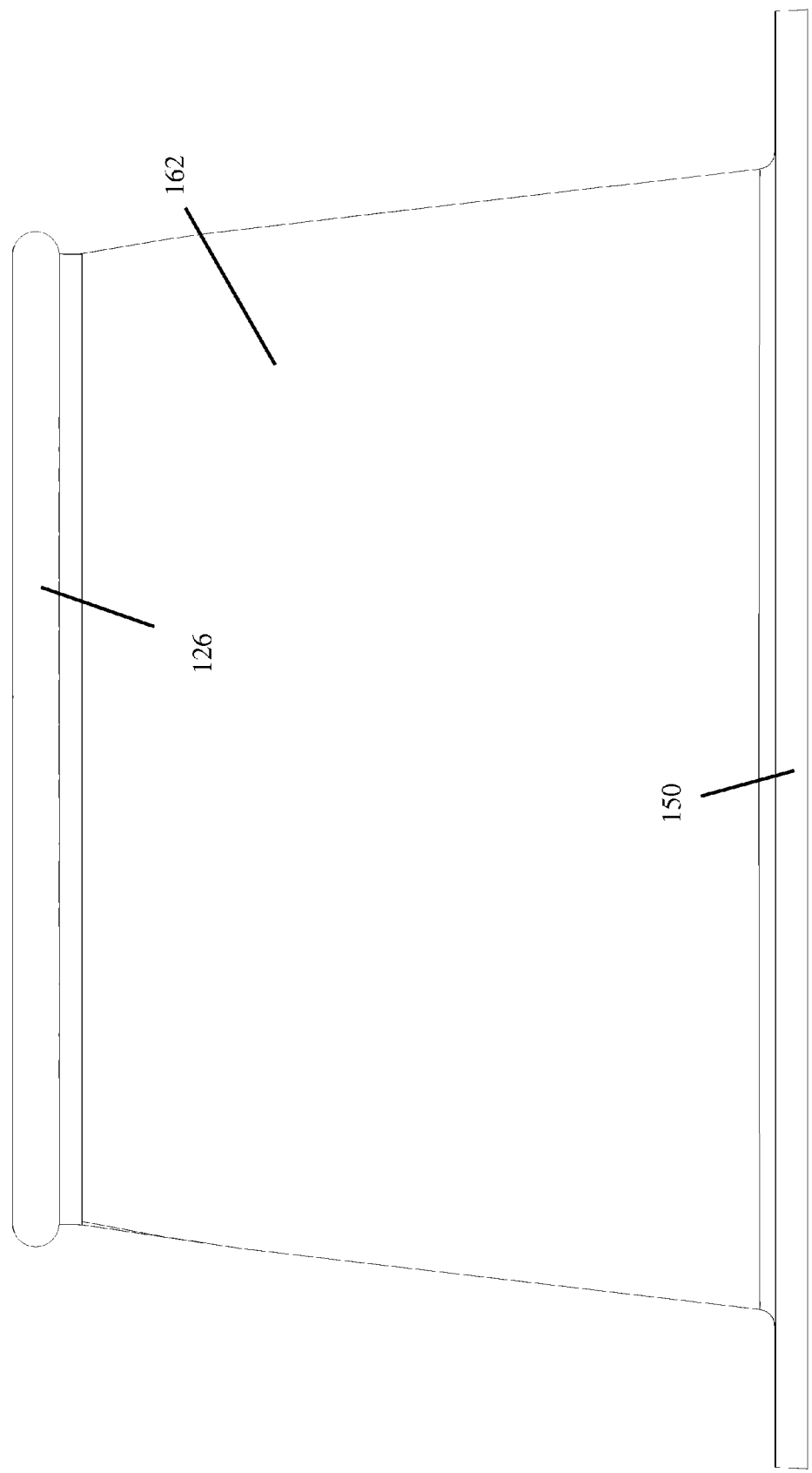
FIG. 15 is a bottom view thereof.

FIG. 14 shows a top view of the toggle head 166 within toggle aperture 148. Toggle head 166 is sized to pass into toggle aperture 148. The toggle head 166 may be adjusted to a position exterior of the retainer aperture 128 as shown in FIG. 18.

Figure 16:
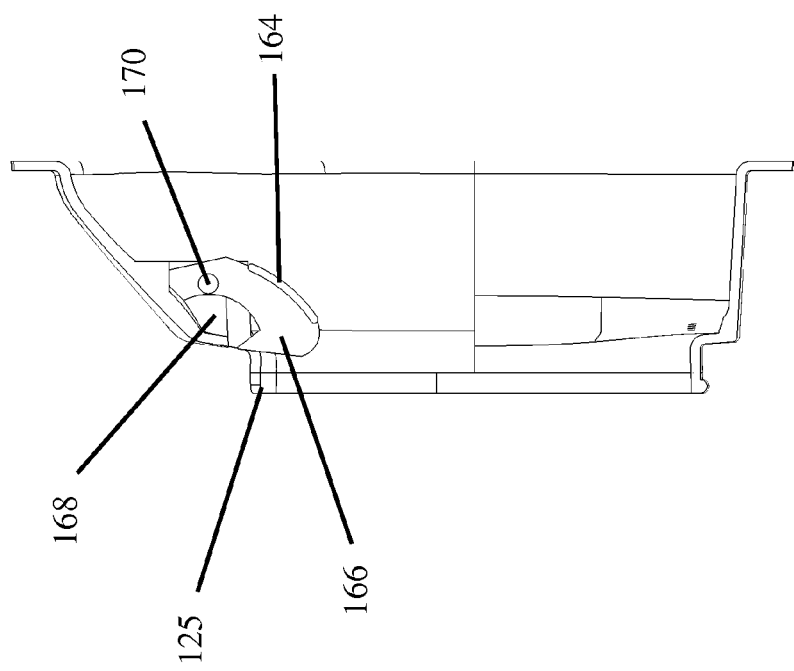
FIG. 16 is a sectional view thereof.
Figure 17:
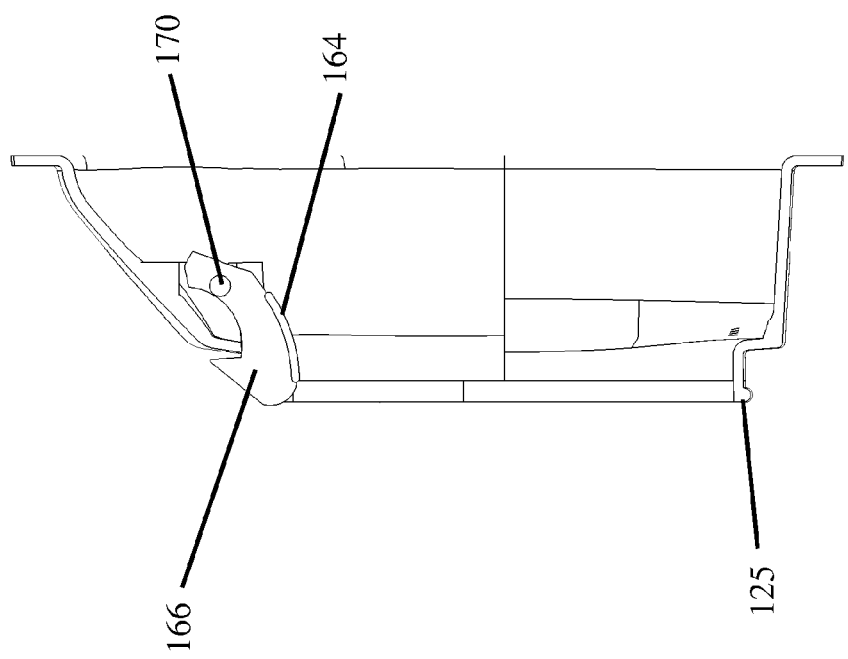
FIG. 17 is a sectional view thereof.
Figure 18:
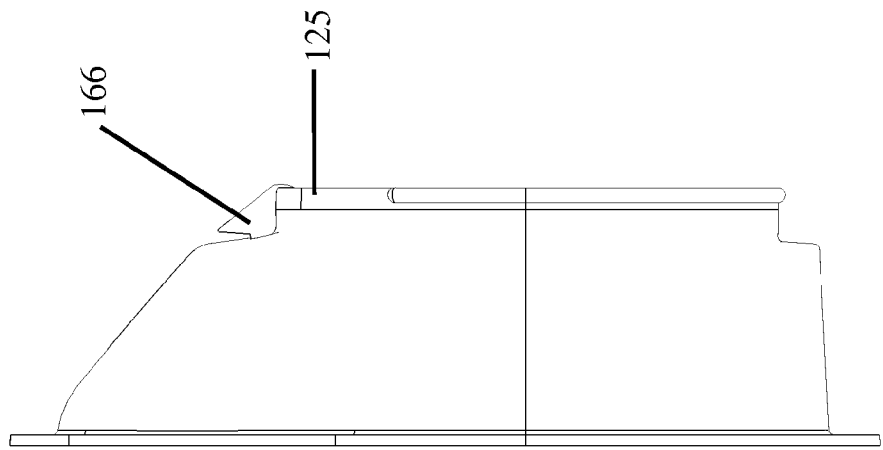
FIG. 18 is a left side view of a glove retainer of one embodiment of the present invention.
Figure 19:
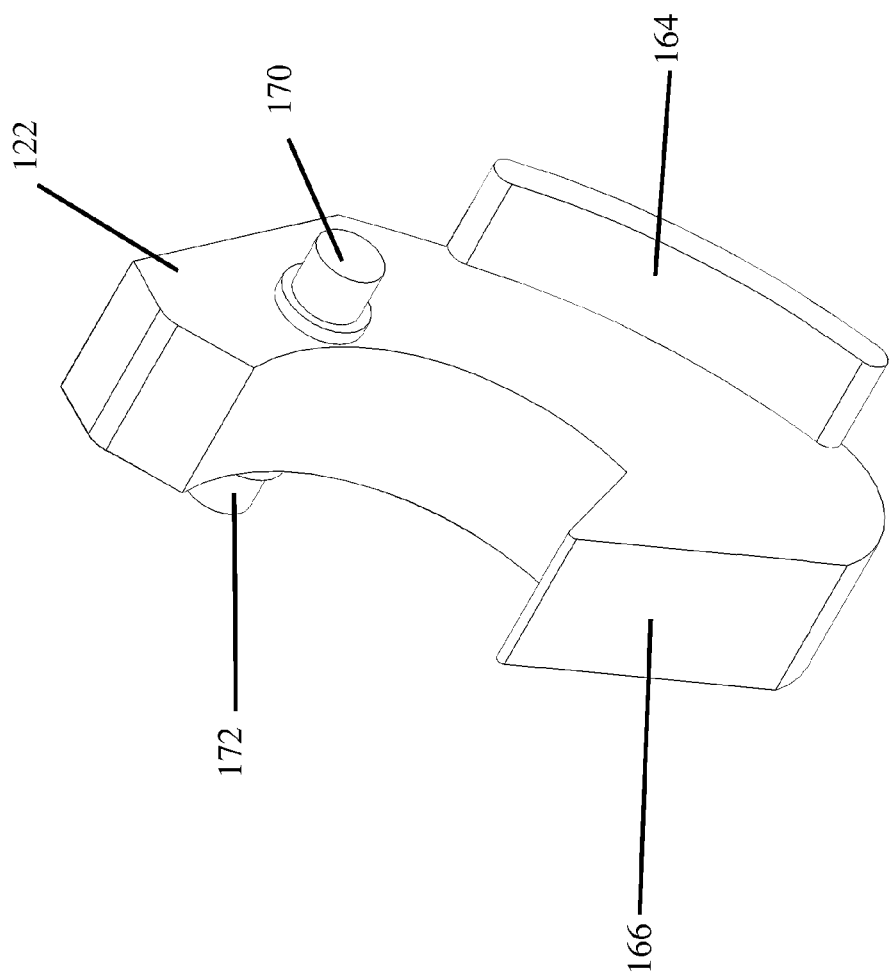
FIG. 19 is a perspective view of a release toggle of one embodiment of the present invention.
Figure 20:
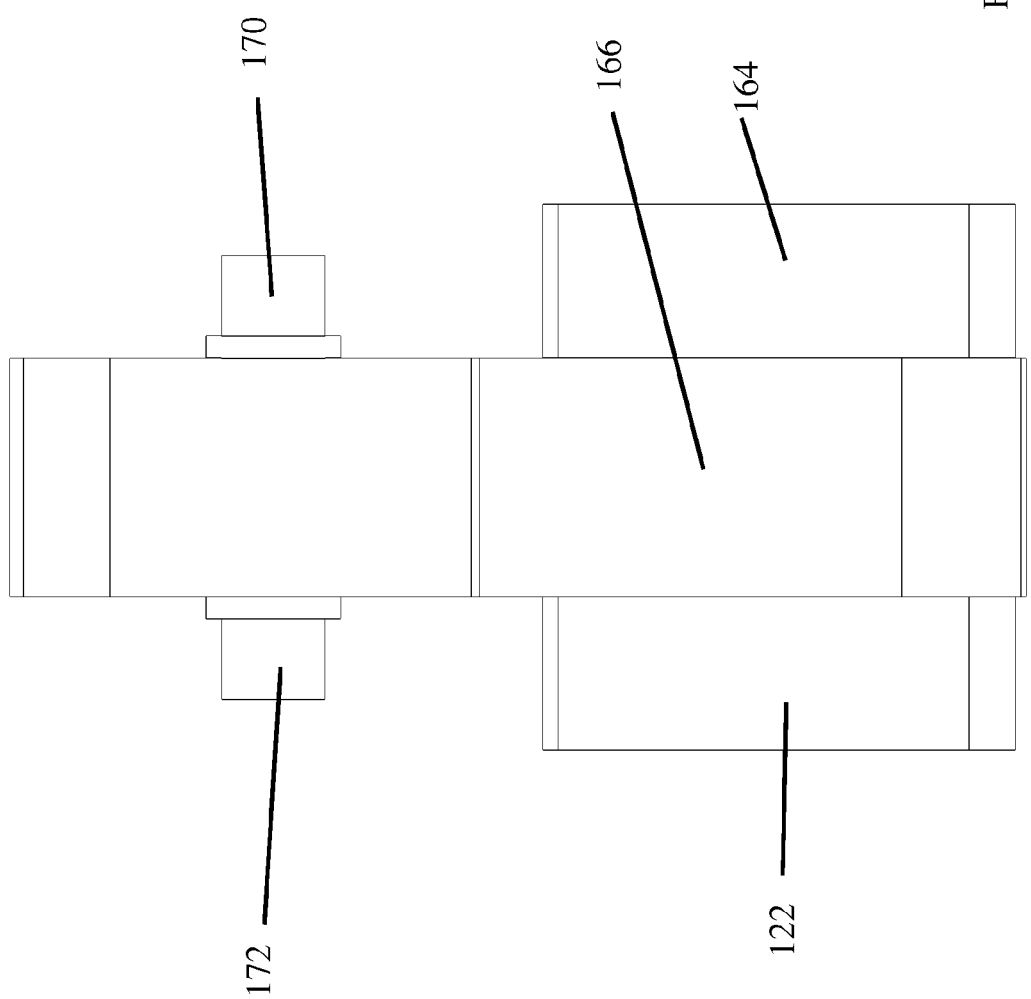
FIG. 20 is a front view thereof.
Figure 21:
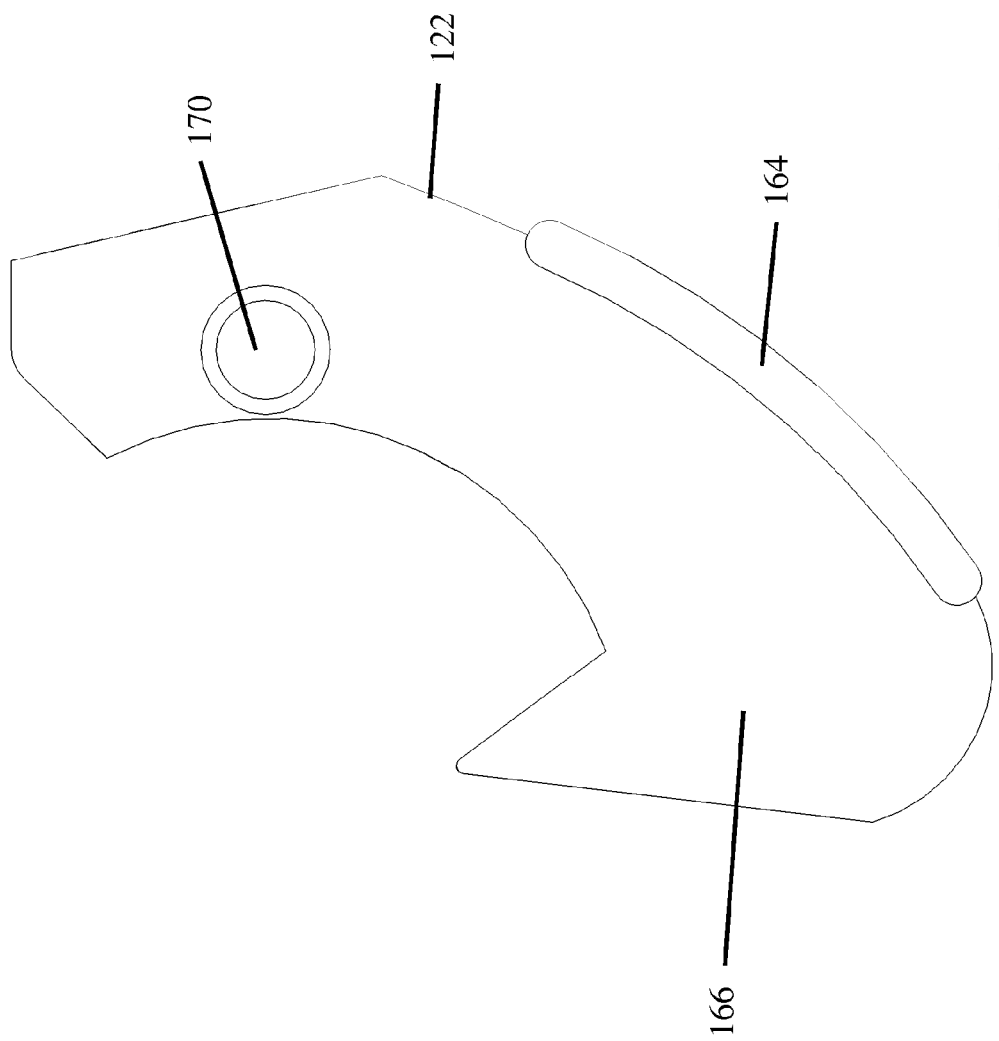
FIG. 21 is a right side view thereof, the left side view being a mirror image of the right side view.
Figure 22:
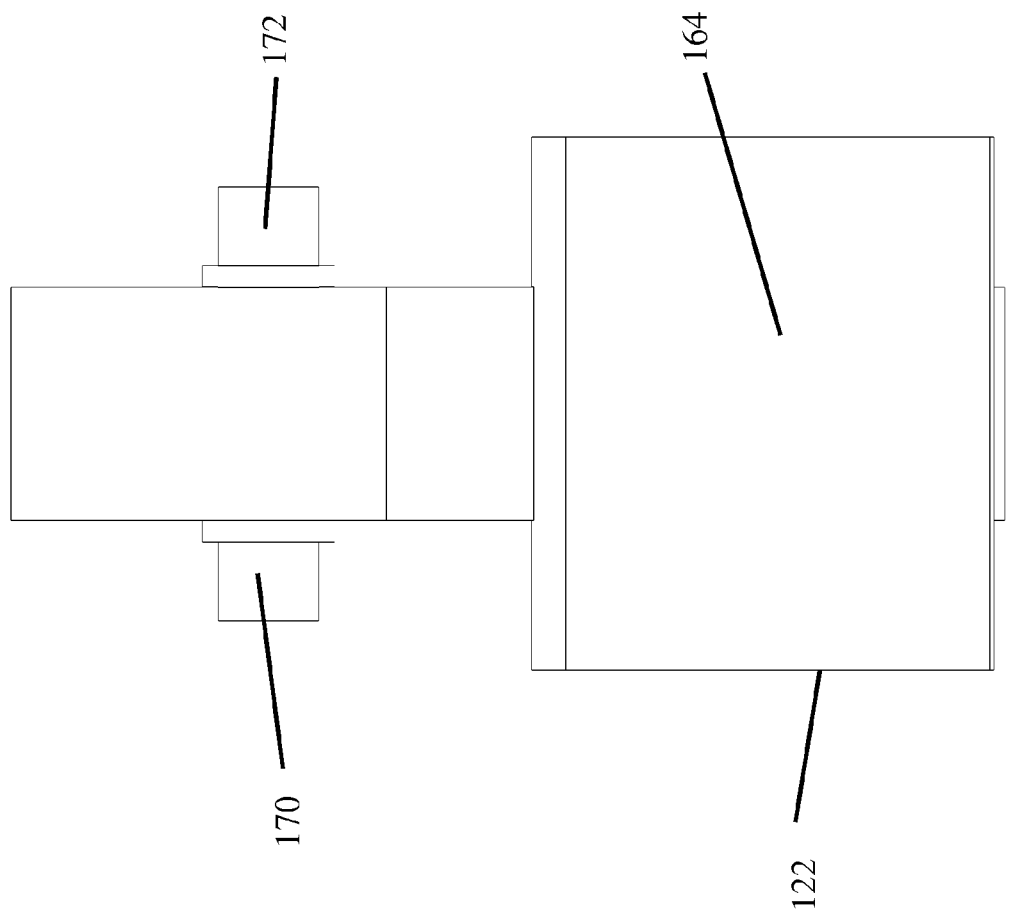
FIG. 22 is a rear view thereof.
Figure 23:
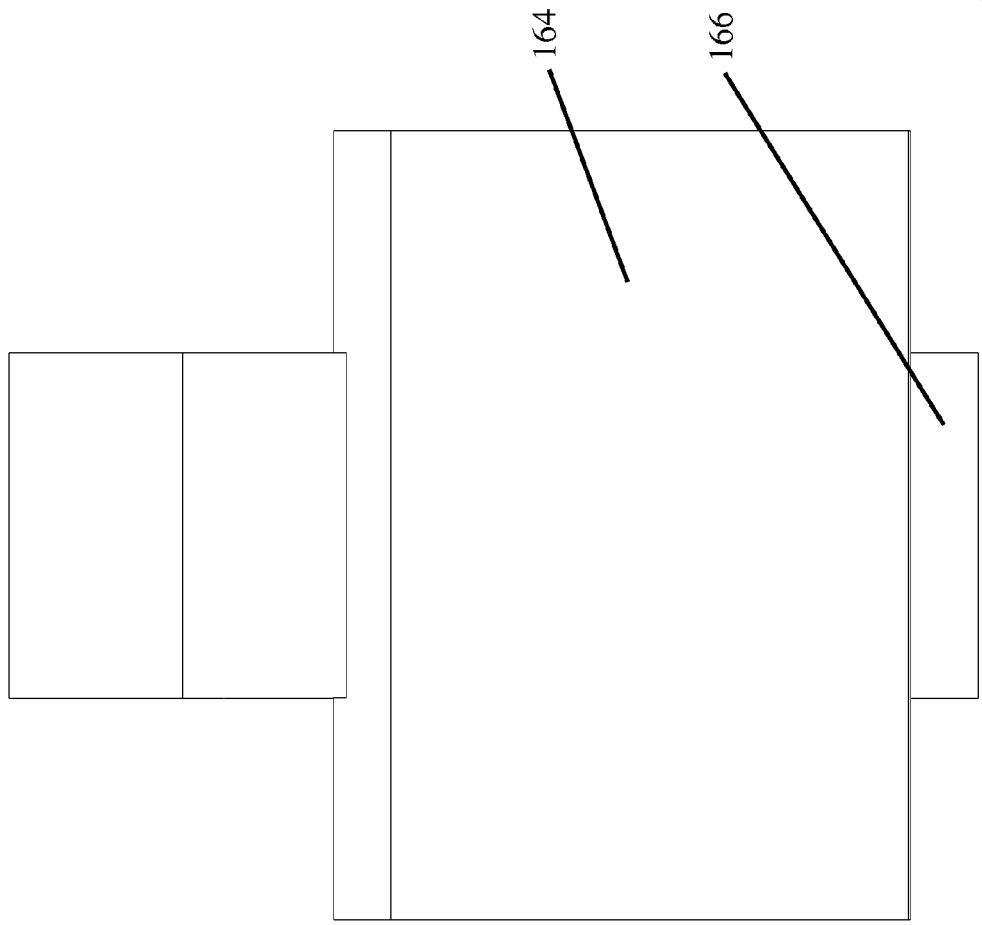
FIG. 23 is a bottom view thereof.
Figure 24:
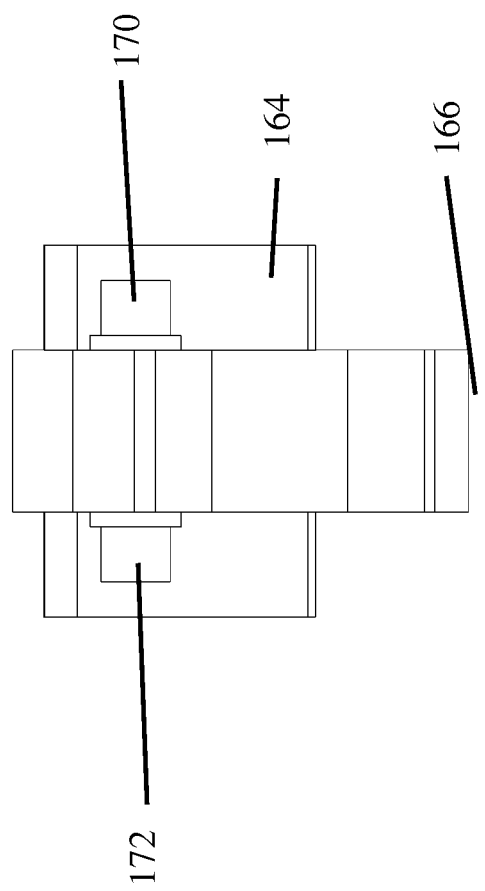
FIG. 24 is a top view thereof.

FIGS. 16-18 show a sectional view of the release toggle 122 within glove retainer 116. Pivot fingers 170, 172 are secured within toggle receiver 168. Toggle head 166 passes in and out of toggle aperture 148 as shown in FIGS. 17-18. In one embodiment, release toggle 122 pivotally attaches to the glove retainer 116. The release toggle 122 pivots up and down to extend above the opening created by toggle aperture 148. Movement of the release toggle 122 upwards breaks the plane of the toggle aperture 148 and extends above the retainer aperture 128. The release toggle 122 pushes at least a portion of the glove off the glove retainer 116 thus releasing the glove from the glove retainer 116.

FIGS. 19-24 show the release toggle 122 of one embodiment. Pivots 170, 172 secure within toggle receiver 168. Toggle head 166 provides a raised surface that can extend beyond toggle aperture 148. Toggle shoulder 164 extends to the side of the toggle head 166 to increase the width of the release toggle 122. The width of the release toggle 122 is greater than the width of the toggle aperture 148 to limit the pivoting of the release toggle 122.

The control panel 120 activates the motor 154 to create the vacuum. The speed of the motor controls the pressure applied within the vacuum chamber to the glove. The user may increase the speed of the motor to apply a greater pressure to the glove. The user may decrease the speed of the motor to apply a lesser pressure to the glove. One embodiment allows full customization of the speed of the motor to allow the user to operate the machine at his preferences.

In one embodiment, motor is a 120 V electric motor. The motor provides an orifice of 1.250 inches. The specification of the motor of one embodiment is 1.250 inch orifice, 6.9 amps, 811 Watts, 34,820 RPM, 17.3 Vac (in H2O), 83.5 Flow in CFM, and 170 Air Watts. The motor may be an AC motor or a DC motor.

The user may also control the time period for which the motor is activated. The motor must be activated for sufficient time to allow the user to insert his/her hand into the glove.

Some users may require additional time to apply the gloves. The user may adjust the duration of the activation of the motor at control panel 120.

In one embodiment, the control panel 120 may be in communication with a computing device and storage that allows each user to store his/her preferences. The user may select his/her user name for the device. The motor will then activate according to the user's stored preferences. The system may store multiple settings defining the time period for which the motor is activated and the speed of the motor. The user may select the setting and activate the motor according to the defined settings.

Figure 25:
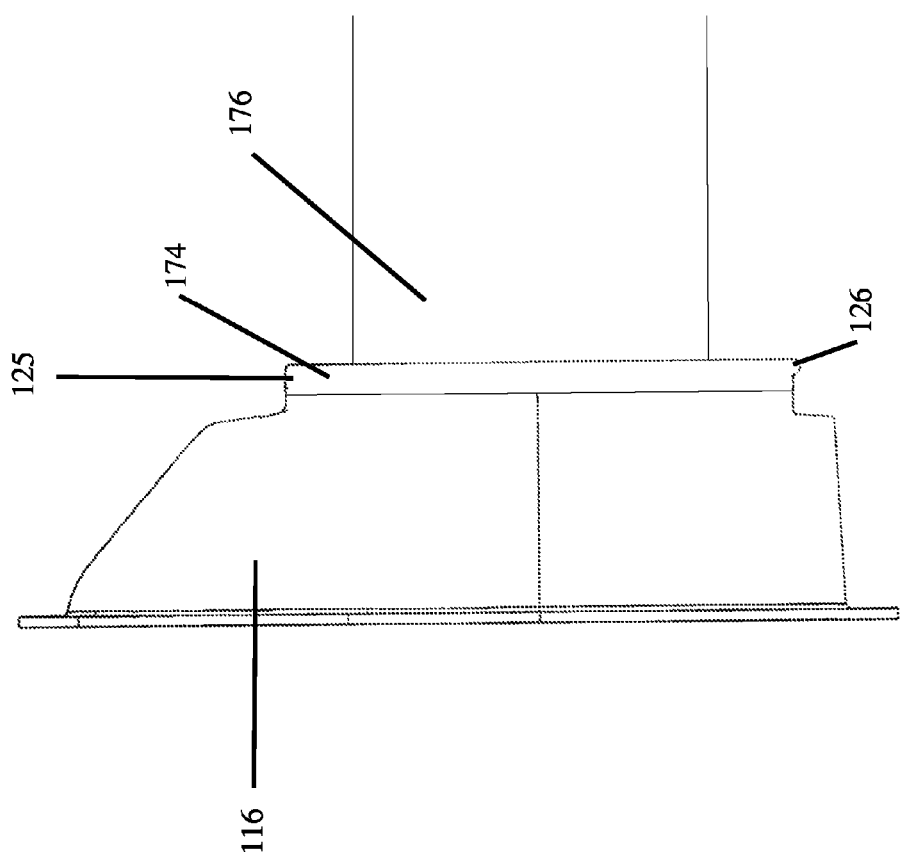
FIG. 25 is a left side environmental view of one embodiment of the present invention.
Figure 26:
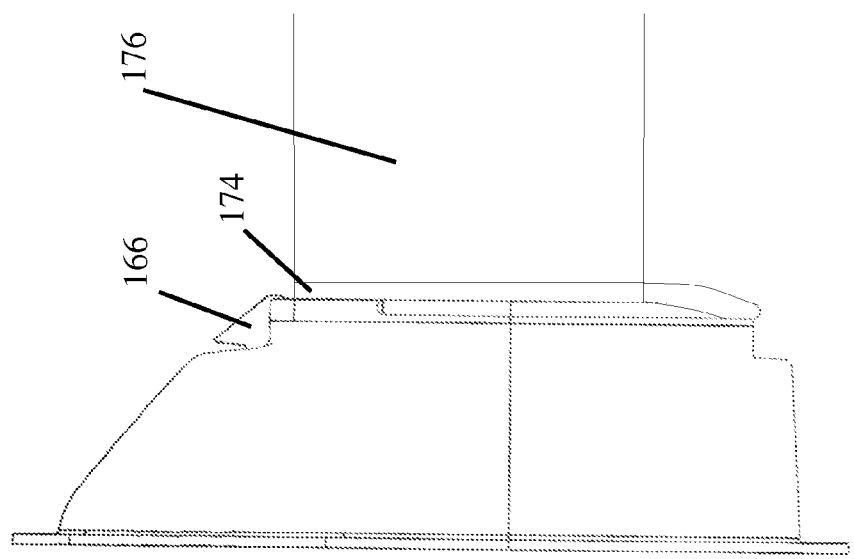
FIG. 26 is a left side view thereof.
Figure 27:
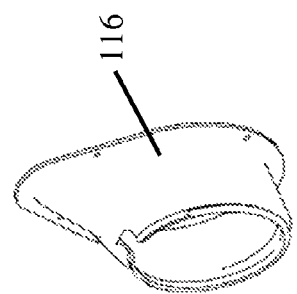
FIG. 27 is a top side view of a glove retainer of one embodiment of the present invention.
Figure 28:
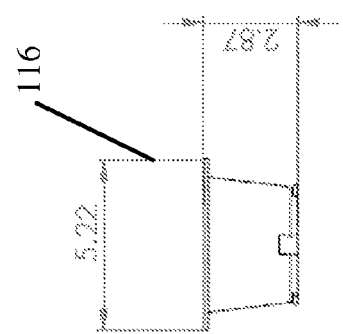
FIG. 28 is a perspective view thereof.
Figure 30:
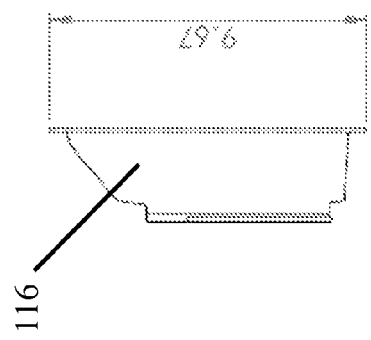
FIG. 30 is a right side view thereof, the left side view being a mirror image of the right side view.
Figure 29:
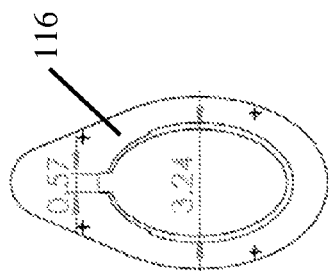
FIG. 29 is a front view thereof.
Figure 31:
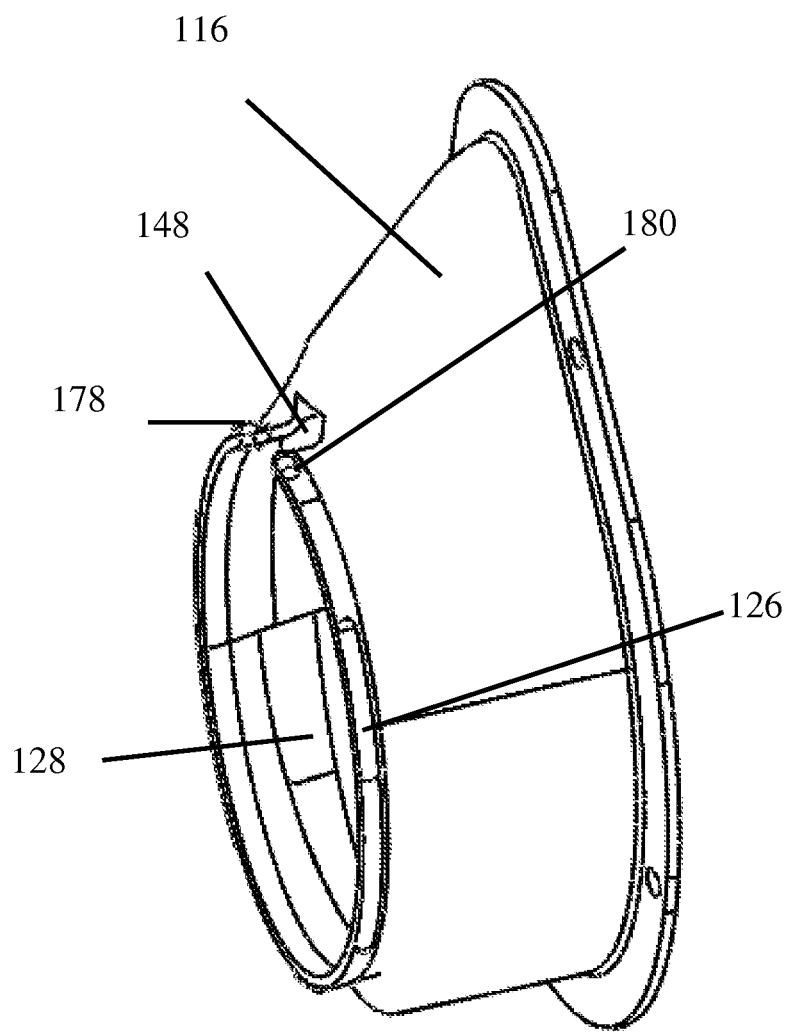
FIG. 31 is a perspective of a glove retainer of one embodiment of the present invention.
Figure 32:
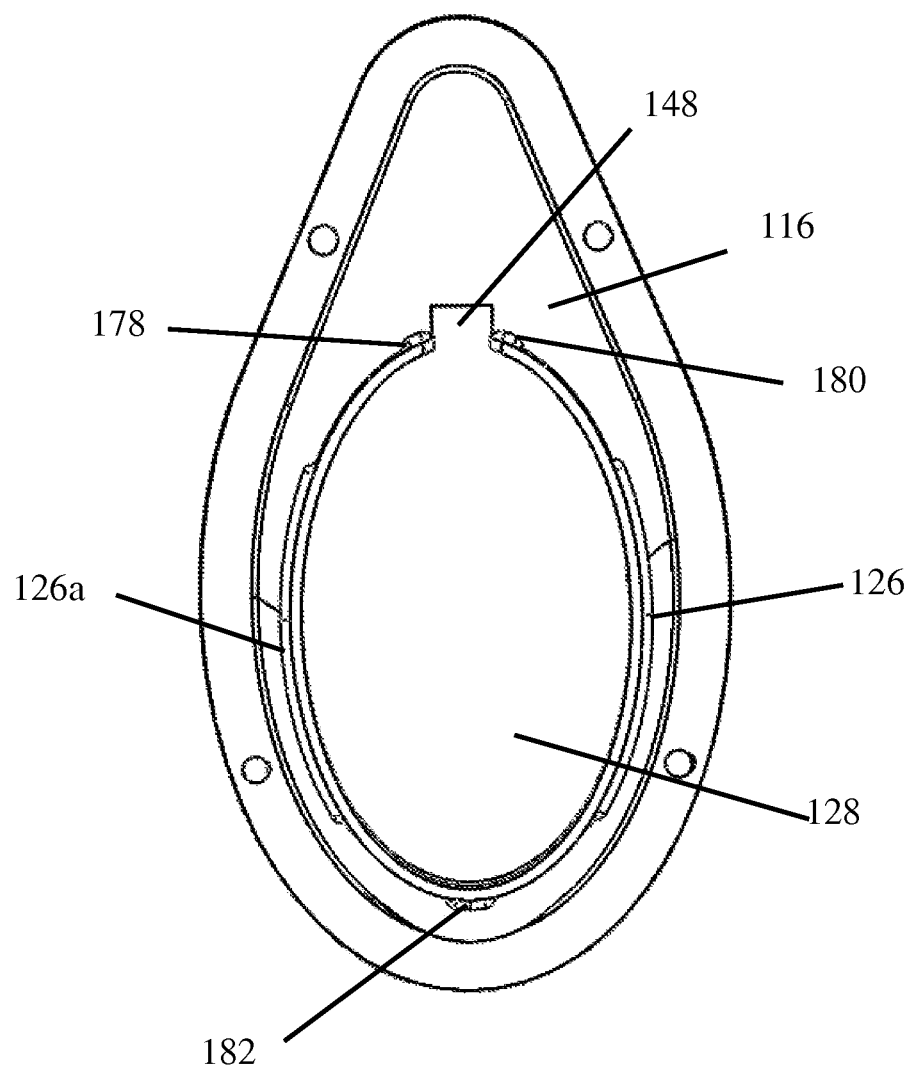
FIG. 32 is a front view thereof.
Figure 33:
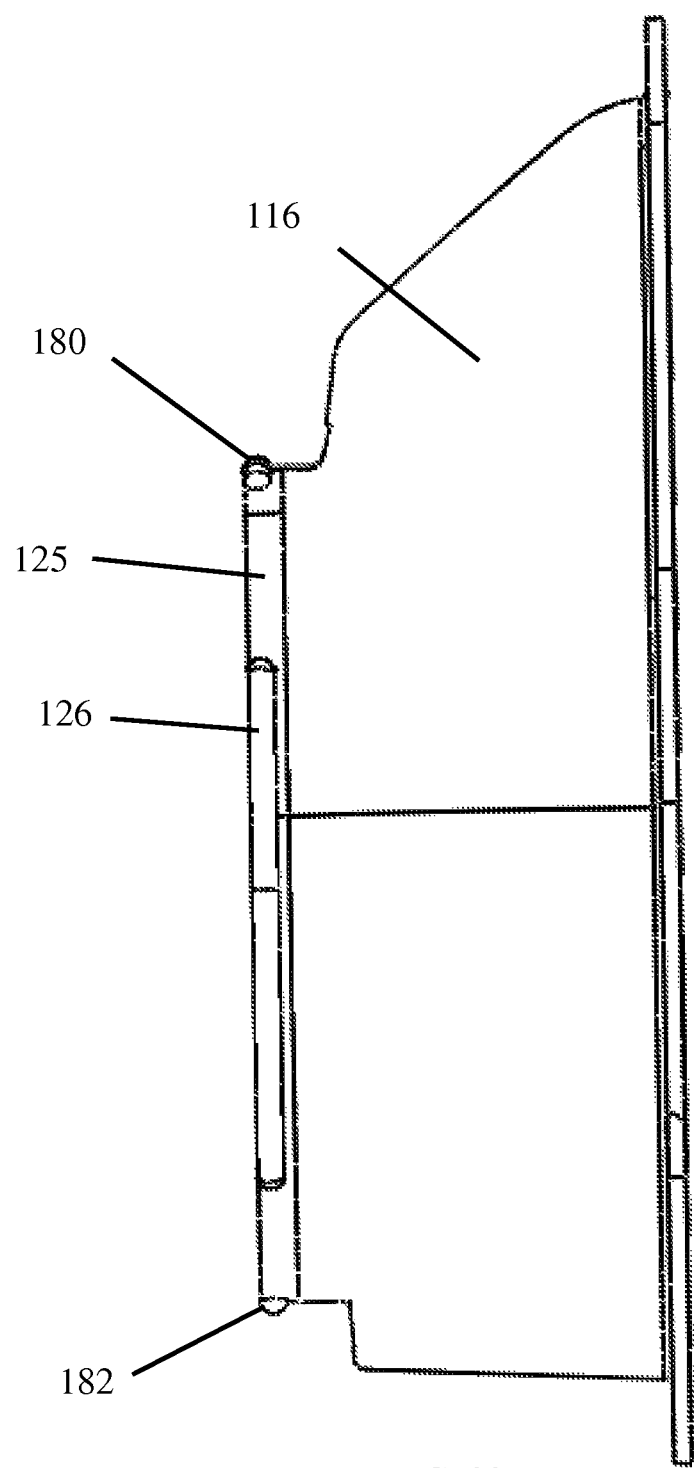
FIG. 33 is a right side view thereof, the left side view being a mirror image of the right side view.
Figure 34:
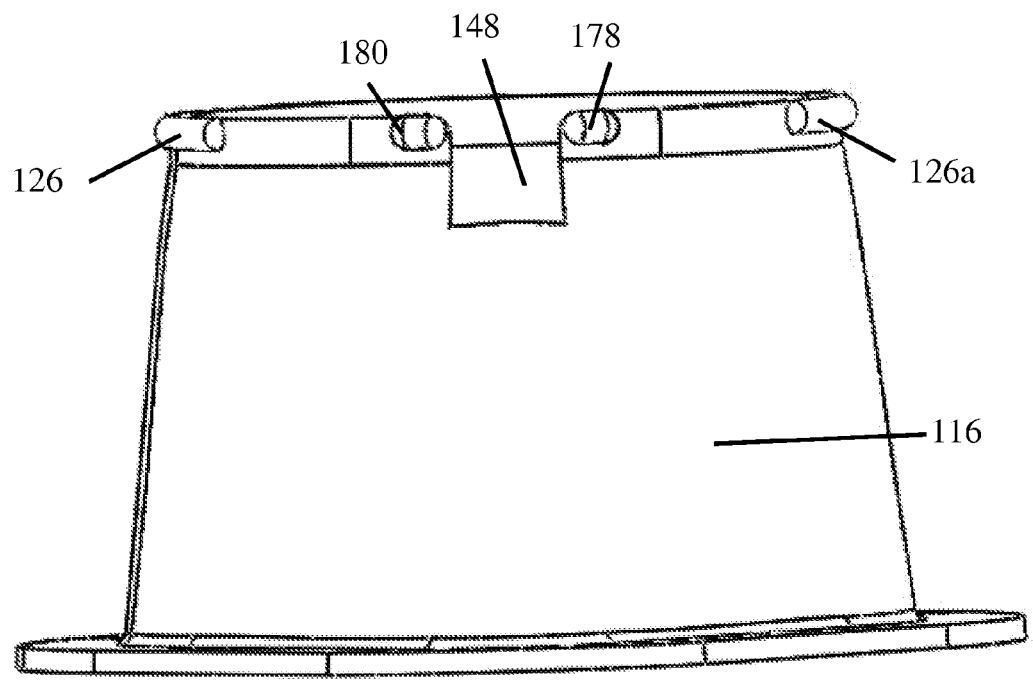
FIG. 34 is a top view thereof.
Figure 35:
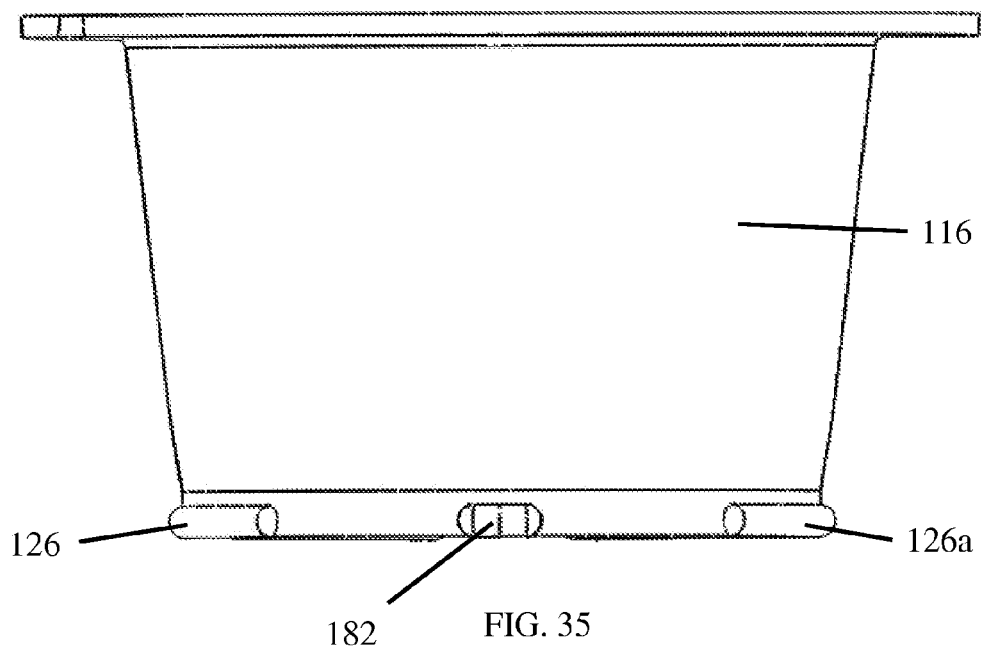
FIG. 35 is a bottom view thereof.

FIGS. 25 and 26 show the operation of the glove dispensing device 100. The user installs a glove 174 on glove retainer 116. The glove may be installed with the thumb in an upward direction to orient the glove with the user's hand. The glove is placed over lip 126 and collar 125. When installing the glove 174, the release toggle 122 is positioned in the secure position. In one embodiment, the release toggle 122 is biased to the secure position by a biasing device such as a spring or other biasing element. In one embodiment, gravity causes the release toggle 122 to be biased to the secure position. The release toggle 122 in the secure position allows the glove 174 to be secured to glove retainer 116. The release toggle 122 of one embodiment in the secure position is positioned not to interfere with installing the glove 174 on collar 125 or lip 126. In one embodiment, the toggle head 166 in the secure position is located within the retainer aperture 128, collar 125, and lip 126. In one embodiment, the toggle head 166 is located below the collar 125 when in the secure position.

The user may then activate the vacuum. In one embodiment, the motor activates creating the vacuum. The glove is inverted and drawn into retainer aperture 128. Lip 126 and collar 125 maintain the glove on the glove retainer 116. The user 176 may then place his/her hand into the retainer aperture 128. The user orients his/her hand with the glove to insert the user's fingers properly into the glove.

Referring to FIG. 26, the user 176 then directs his/her hand towards release toggle 122. The user adjusts the release toggle 122 to a release position which releases the glove 174 from collar 125. In one embodiment, the user presses upwards to adjust the release toggle 122 into the release position. In this embodiment, the toggle head 166 raises above the collar 125 and lip 126 when in the release position. The toggle head 166 in the release position is located outside of the retainer aperture 128, collar 125, and lip 126.

When positioned into the release position, the release toggle 122 contacts glove 174 and forces glove off of collar 125. The toggle aperture 148 enables the release toggle 122 to remove the glove 174 off of collar 125 as shown in FIG. 26. The movement of the glove 174 by toggle head 166 assists with the removal of the glove 174 from glove retainer 116. Once removed from collar 125, the glove 174 is released onto the user's hand such that the glove is applied to the user's hand.

FIGS. 27-30 show the glove retainer 116 of one embodiment of the present invention. The glove retainer 116 of one embodiment provides an oval shaped retainer aperture. The retainer aperture should be sized large enough for a user to insert his/her hand into the retainer aperture. The retainer aperture may have a width ranging from 1 to 10 inches, preferable 3.24 inches. The retainer aperture may have a height ranging from 3 to 20 inches, preferably 4 to 9 inches.

FIGS. 31-35 show another embodiment of the glove retainer 116 that utilizes retention fingers 178, 180, 182 that position the glove while the motor is activated. Glove retainer 116 also provides collar 125 and lips 126, 126a. In one embodiment, lips 126, 126a and retention fingers 178, 180, 182 protrude outward from the collar 125. Lips 126, 126a and retention fingers 178, 180, 182 provide additional surface for the glove to grip when installed on the glove retainer 116. The increased friction caused by lips 126, 126a and retention fingers 178, 180, 182 maintain the position of the glove when the motor is activated to prevent the glove from being vacuumed into retainer aperture 128.

In one embodiment, retention fingers 178, 180, 182 are protrusions that extend away from the retention aperture 128. Retention fingers 178, 180 are located adjacent the toggle aperture 148 to secure the glove at the toggle. These retention fingers 178, 180, 182 function with the lips 126, 126a to grip the glove while the present invention is in use.

From the foregoing, it will be seen that the present invention is one well adapted to obtain all the ends and objects herein set forth, together with other advantages which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A glove dispensing device for retaining a glove in an open position for placement of the glove on a hand, the device comprising:
   a housing;
   a glove retainer extending outward from the housing;
   a retainer aperture located at least partially within the glove retainer;
   a motor venting gas from the retainer aperture; and
   a release toggle attached to the housing wherein the release toggle adjusts to a position in which at least a portion of the release toggle is located external of the glove retainer.

2. The device of claim 1 further comprising:
   the release toggle attached to the housing, the release toggle adjustable from a from a first position wherein the release toggle is located within the housing; and
   the release toggle adjustable to a second position wherein the release toggle is at least partially located externally of the housing.

3. The device of claim 1 further comprising:
   a toggle aperture of the glove retainer; and
   the release toggle sized to at least partially pass through the toggle aperture.

4. The device of claim 3 wherein the release toggle is pivotally attached to the housing.

5. The device of claim 3, the release toggle comprising:
   a toggle head sized to at least partially pass through the toggle aperture;
   the release toggle adjustable from a first position wherein the release toggle is located within the housing; and
   the release toggle adjustable to a second position wherein the release toggle is at least partially located externally of the housing.

6. The device of claim 5, the release toggle comprising:
   a toggle shoulder wherein the toggle shoulder is sized not to pass through the toggle aperture, the toggle shoulder extending horizontally outward from the toggle head to limit movement of the release toggle.

7. The device of claim 1 further comprising:
a vacuum chamber located within the housing adjacent the glove retainer; and
the vacuum transferring gas from the vacuum chamber to outside of the housing.

8. The device of claim 1 further comprising:
an intake chamber separated from the vacuum chamber, the intake chamber venting gas from the vacuum chamber to outside of the housing.

9. The device of claim 8 further comprising:
a vacuum release aperture within the vacuum chamber; the vacuum release providing a pathway for gas to flow from the vacuum chamber to outside of the housing.

10. The device of claim 8 further comprising:
an exhaust within the intake chamber, the exhaust providing a pathway for gas to flow from the intake chamber to outside of the housing.

11. The device of claim 1 further comprising:
a controller that regulates the strength of the vacuum and the time period for activating the vacuum wherein the strength and time period are dependent upon a user defined input.

12. The device of claim 11 further comprising:
a motor forming the vacuum;
the controller regulating the speed of the motor; and
the controller regulating the time period that the motor is activated.

13. A glove dispensing device for retaining a glove in an open position for placement of the glove on a hand, the device comprising:
a housing;
a glove retainer extending outward from the housing;
a retainer aperture located at least partially within the glove retainer;
a vacuum chamber located within the housing adjacent the glove retainer wherein gas flows from the retainer aperture through the vacuum chamber; and
a release toggle attached to the housing wherein the release toggle adjusts to a position in which at least a portion of the release toggle is located external of the glove retainer.

14. The device of claim 13 further comprising:
an intake chamber separated from the vacuum chamber, the intake chamber venting gas from the vacuum chamber to outside of the housing.

15. The device of claim 13 further comprising:
a controller that regulates the speed of the motor and the time period for activating the motor wherein the speed and time period are dependent upon a user defined input.

16. The device of claim 13 further comprising:
the release toggle attached to the housing, the release toggle adjustable from a from a first position wherein the release toggle is located within the housing; and
the release toggle adjustable to a second position wherein the release toggle is at least partially located externally of the housing.

17. The device of claim 16 further comprising:
a toggle aperture of the glove retainer; and
the release toggle sized to at least partially pass through the toggle aperture.

18. A glove dispensing device for retaining a glove in an open position for placement of the glove on a hand, the device comprising:
a housing;
a glove retainer extending outward from the housing;
a retainer aperture of the glove retainer wherein the retainer aperture provides an opening into the housing through the glove retainer wherein gas is vented from the retainer aperture; and
a release toggle attached to the housing wherein the release toggle adjusts to a position in which at least a portion of the release toggle is located external of the glove retainer.

19. The device of claim 18 further comprising:
a toggle aperture of the glove retainer wherein the toggle aperture is an opening in the glove retainer;
the release toggle sized to at least partially pass through the toggle aperture;
a toggle head of the release toggle sized to at least partially pass through the toggle aperture;
the release toggle adjustable from a first position wherein the release toggle is located within the collar;
the release toggle adjustable to a second position wherein the release toggle is at least partially located externally of the collar when the release toggle is adjusted to the second position.

20. The device of claim 19 wherein the release toggle pivotally attaches to the housing wherein the toggle head extends above the toggle aperture when the release toggle is adjusted to the second position.

* * * * *